(12) United States Patent
Hyodo et al.

(10) Patent No.: US 11,266,321 B2
(45) Date of Patent: Mar. 8, 2022

(54) VITAL SIGN PROCESSING DEVICE, VITAL SIGN PROCESSING METHOD, AND INFORMATION PROCESSING DEVICE

(71) Applicant: SONY CORPORATION, Tokyo (JP)

(72) Inventors: Yasuhide Hyodo, Tokyo (JP); Takanori Ishikawa, Saitama (JP)

(73) Assignee: SONY CORPORATION, Tokyo (JP)

( * ) Notice: Subject to any disclaimer, the term of this patent is extended or adjusted under 35 U.S.C. 154(b) by 407 days.

(21) Appl. No.: 16/328,563

(22) PCT Filed: Aug. 23, 2017

(86) PCT No.: PCT/JP2017/030042
§ 371 (c)(1),
(2) Date: Feb. 26, 2019

(87) PCT Pub. No.: WO2018/055969
PCT Pub. Date: Mar. 29, 2018

(65) Prior Publication Data
US 2021/0290092 A1    Sep. 23, 2021

(30) Foreign Application Priority Data

Sep. 26, 2016 (JP) .............................. JP2016-186623

(51) Int. Cl.
*A61B 5/00* (2006.01)
*A61B 5/024* (2006.01)

(52) U.S. Cl.
CPC ........ *A61B 5/02438* (2013.01); *A61B 5/7203* (2013.01); *A61B 5/7221* (2013.01); *A61B 5/7225* (2013.01)

(58) Field of Classification Search
CPC . A61B 5/02438; A61B 5/7203; A61B 5/7221; A61B 5/7225; A61B 5/02; A61B 5/0245
See application file for complete search history.

(56) References Cited

U.S. PATENT DOCUMENTS

| 4,955,379 A | 9/1990 | Hall |
| 2007/0060827 A1 | 3/2007 | Kobayashi et al. |

(Continued)

FOREIGN PATENT DOCUMENTS

| EP | 0303502 A1 | 2/1989 |
| EP | 1757225 A1 | 2/2007 |

(Continued)

OTHER PUBLICATIONS

International Search Report and Written Opinion of PCT Application No. PCT/JP2017/030042, dated Nov. 37, 2017, 08 pages of ISRWO.

(Continued)

*Primary Examiner* — George Manuel
(74) *Attorney, Agent, or Firm* — Chip Law Group

(57) ABSTRACT

A vital sign processing device according to an embodiment of the present technology includes a pulse-wave sensor unit, an output unit, and a first filter unit. The pulse-wave sensor unit outputs a pulse-wave signal. The output unit outputs a heart-rate information item on the basis of the output pulse-wave signal. The first filter unit sets a first frequency band on the basis of the output heart-rate information item, and allows the set first frequency band of the pulse-wave signal to pass through the first filter unit.

18 Claims, 24 Drawing Sheets

(56) References Cited

U.S. PATENT DOCUMENTS

| | | | |
|---|---|---|---|
| 2009/0227879 A1 | 9/2009 | Matsumoto | |
| 2011/0098582 A1 | 4/2011 | Takahashi et al. | |
| 2012/0283581 A1* | 11/2012 | Olde | A61B 5/0816 600/485 |
| 2015/0208964 A1* | 7/2015 | Addison | A61B 5/14551 600/324 |

FOREIGN PATENT DOCUMENTS

| | | |
|---|---|---|
| GB | 2208709 A | 4/1989 |
| JP | 01-153139 A | 6/1989 |
| JP | 02-172443 A | 7/1990 |
| JP | 11-276448 A | 10/1999 |
| JP | 2007-054471 A | 3/2007 |
| JP | 2009-207810 A | 9/2009 |
| JP | 2011-092236 A | 5/2011 |
| JP | 2011-115459 A | 6/2011 |
| JP | 2014-094043 A | 5/2014 |
| WO | 2007/046283 A1 | 4/2007 |

OTHER PUBLICATIONS

Office Action for JP Patent Application No. 2018-540922 dated Mar. 3, 2021, 03 pages of Office Action.

* cited by examiner

| Filter ID | Heart-rate range | Filter coefficient |
|---|---|---|
| 1 | 40 [bpm] ≦ hr < 55 [bpm] | BScoef_vector1 |
| 2 | 55 [bpm] ≦ hr < 65 [bpm] | BScoef_vector2 |
| ... | ... | ... |
| N | 180 [bpm] ≦ hr < 200 [bpm] | BScoef_vectorN |

FIG.10

| Filter ID | Heart-rate range | Filter coefficient |
|---|---|---|
| 1 | 40 [bpm] ≦ hr < 55 [bpm] | BPcoef_vector1 |
| 2 | 55 [bpm] ≦ hr < 65 [bpm] | BPcoef_vector2 |
| ... | ... | ... |
| N | 180 [bpm] ≦ hr < 200 [bpm] | BPcoef_vectorN |

FIG.15

VITAL SIGN PROCESSING DEVICE, VITAL SIGN PROCESSING METHOD, AND INFORMATION PROCESSING DEVICE

CROSS REFERENCE TO RELATED APPLICATIONS

This application is a U.S. National Phase of International Patent Application No. PCT/JP2017/030042 filed on Aug. 23, 2017, which claims priority benefit of Japanese Patent Application No. JP 2016-186623 filed in the Japan Patent Office on Sep. 26, 2016. Each of the above-referenced applications is hereby incorporated herein by reference in its entirety.

TECHNICAL FIELD

The present technology relates to a vital sign processing device that outputs heart-rate information items of a user, a vital sign processing method, and an information processing device.

BACKGROUND ART

In recent years, following trends of health-care and fitness, wristwatch-type or wristband-type devices equipped with a heart-rate sensor for heart-rate training have been developed. Many of these measurement devices employ photoplethysmography (hereinafter, abbreviated as "PPG").

Patent Literature 1 describes a pulsimeter including a pulse-wave sensor and a body-motion sensor. In this pulsimeter, there is provided an adaptive filter that uses, as a monitoring signal, a pulse-wave signal to be output from the pulse-wave sensor, and receives, as an input signal, a body-motion signal to be output from the body-motion sensor. A predictive value of a body-motion component to be calculated by the adaptive filter is subtracted from the pulse-wave signal, and a Fast Fourier Transform (FFT) process is executed on a resultant residual signal. A component at a highest level is extracted as a pulse-wave component from resultant frequency components. With this, a pulse rate per minute is calculated. In this way, the pulse rate is accurately measured (refer, for example, to paragraphs [0007] to [0012] of the specification and FIG. 1 of Patent Literature 1).

CITATION LIST

Patent Literature

Patent Literature 1: Japanese Patent Application Laid-open No. 11-276448

DISCLOSURE OF INVENTION

Technical Problem

Technologies that enable highly accurate heart-rate measurement in this way have been demanded. For example, it is desired that a heart-rate fluctuation can be measured with high accuracy in accordance with various scenes in daily life.

In view of such circumstances, the present technology has been made to provide a vital sign processing device, a vital sign processing method, and an information processing device that enable highly accurate heart-rate measurement.

Solution to Problem

In order to achieve the above-mentioned object, according to an embodiment of the present technology, there is provided a vital sign processing device including a pulse-wave sensor unit, an output unit, and a first filter unit.

The pulse-wave sensor unit outputs a pulse-wave signal.

The output unit outputs a heart-rate information item on the basis of the output pulse-wave signal.

The first filter unit
sets a first frequency band on the basis of the output heart-rate information item, and
allows the set first frequency band of the pulse-wave signal to pass through the first filter unit.

In this vital sign processing device, the first filter unit filters the pulse-wave signal on the basis of the heart-rate information item. A highly accurate heart-rate information item is output on the basis of the filtered pulse-wave signal. In this way, highly accurate heart-rate measurement can be performed.

The first filter unit may set the first frequency band on the basis of a heart rate included in the heart-rate information item.

In this way, the first frequency band is set on the basis of a previous heart rate, and hence the heart-rate information item can be output with high accuracy.

The first filter unit
may include a first filter bank including a plurality of band-pass filters, and
may select, on the basis of the heart rate and from the first filter bank, a filter that allows the first frequency band to pass through the filter.

By using the filter bank in this way, the pulse-wave signal can be easily filtered.

The vital sign processing device may further include a plurality of calculation units each of which calculates a heart-rate-candidate information item and a reliability of the heart-rate-candidate information item on the basis of the output pulse-wave signal.

In this case, the output unit may output the heart-rate information item on the basis of the heart-rate-candidate information item and the reliability of the heart-rate-candidate information item, the heart-rate-candidate information item and the reliability being calculated by each of the plurality of calculation units.

With this, highly accurate heart-rate information items can be output. As a result, highly accurate heart-rate measurement can be performed.

Each of the plurality of calculation units may calculate the heart-rate-candidate information item and the reliability of the heart-rate-candidate information item on the basis of the pulse-wave signal filtered by the first filter unit.

By this calculation based on the filtered pulse-wave signal, the heart-rate-candidate information item, for example, can be calculated with high accuracy.

The vital sign processing device may further include:
a body-motion sensor that outputs a body-motion signal; and
a noise-reduction processing unit that separates, on the basis of the body-motion signal, a body-motion noise from the pulse-wave signal output from the pulse-wave sensor unit.

In this case, each of the plurality of calculation units may calculate the heart-rate-candidate information item and the reliability of the heart-rate-candidate information item on the basis of the pulse-wave signal from which the body-motion noise has been separated.

By this calculation based on the pulse-wave signal from which the body-motion noise has been separated, the heart-rate-candidate information item, for example, can be calculated with high accuracy.

The first filter unit may filter the pulse-wave signal from which the body-motion noise has been separated by the noise-reduction processing unit.

With this, the first frequency band of the pulse-wave signal from which the body-motion noise has been separated is allowed to pass, and other bands can be removed. In this way, highly accurate heart-rate measurement can be performed.

The pulse-wave sensor unit may include a plurality of pulse-wave sensors, and may output, as the pulse-wave signal, any one of a plurality of pulse-wave-candidate signals that are generated by the plurality of pulse-wave sensors.

With this, highly accurate heart-rate measurement can be performed.

The vital sign processing device may further include a generating unit that generates, on the basis of the plurality of pulse-wave-candidate signals that are generated by the plurality of pulse-wave sensors, a reference signal for separating the body-motion noise.

In this case, the noise-reduction processing unit may include an adaptive filter to which the reference signal is input as an input signal, and may output an error signal obtained by subtraction of an output value of the adaptive filter from the pulse-wave signal.

With this, the body-motion noise can be reduced with high accuracy.

The vital sign processing device may further include a second filter unit that sets a second frequency band on the basis of the heart-rate information item output by the output unit, and that removes the set second frequency band of the reference signal.

With this, the reference signal can be generated with high accuracy. Thus, the body-motion noise can be reduced with high accuracy.

The second filter unit may set the second frequency band on the basis of a heart rate included in the heart-rate information item.

In this way, the second frequency band is set on the basis of the previous heart rate, and hence the reference signal can be generated with high accuracy.

The second filter unit may include a second filter bank including a plurality of band-elimination filters, and may select, on the basis of the heart rate and from the second filter bank, a filter that removes the second frequency band.

By using the filter bank in this way, the reference signal can be easily filtered.

The second filter unit may filter at least one of the plurality of pulse-wave-candidate signals or the body-motion signal.

In this case, the generating unit may generate the reference signal on the basis of an output from the second filter unit.

By this calculation based on the signal from which the second frequency band has been removed, the reference signal can be calculated with high accuracy.

The generating unit may generate the reference signal on the basis of the plurality of pulse-wave-candidate signals filtered by the first filter unit.

In this case, the noise-reduction processing unit may output an error signal obtained by subtraction of the output value of the adaptive filter from the pulse-wave signal filtered by the first filter unit.

Processes such as the separation of the body-motion noise are executed intensively on a frequency band of the heart rate. With this, the error signal, for example, can be calculated with high accuracy.

The second filter unit may filter the reference signal generated by the generating unit, and may then output the filtered reference signal to the adaptive filter.

As a result, the processes such as the separation of the body-motion noise are executed on the basis of the reference signal from which the second frequency band has been removed. With this, the error signal, for example, can be calculated with high accuracy.

The plurality of pulse-wave sensors may include a pulse-wave-signal pulse-wave sensor that generates the pulse-wave signal by emitting light beams in a predetermined wavelength band and then detecting a reflected light beam among the light beams in the predetermined wavelength band.

In this case, the vital sign processing device may further include a light-intensity control unit that controls, on the basis of the pulse-wave signal filtered by the first filter unit, light intensities of the light beams in the predetermined wavelength band, the light beams being emitted from the pulse-wave-signal pulse-wave sensor.

By controlling the intensities of the light beams that are emitted from the pulse-wave-signal pulse-wave sensor, an intensity of the reflected light beam to be detected, for example, can be properly controlled. Thus, an intensity of the pulse-wave signal, for example, can be controlled with high accuracy.

The light-intensity control unit may control the light intensities of the pulse-wave-signal pulse-wave sensor on the basis of an intensity of a heart-rate signal contained in the pulse-wave signal filtered by the first filter unit, and on the basis of a feedback light intensity that is detected by the pulse-wave-signal pulse-wave sensor.

With this, the intensity of the heart-rate signal contained in the pulse-wave signal can be properly maintained.

The light-intensity control unit may set, on the basis of the intensity of the heart-rate signal, at least one of a target value, a lower-limit value, or an upper-limit value of the feedback light intensity that is detected by the pulse-wave-signal pulse-wave sensor.

With this, the intensity of the heart-rate signal can be properly maintained, and at the same time, the light intensities of the pulse-wave-signal pulse-wave sensor can be controlled with high accuracy.

According to another embodiment of the present technology, there is provided a vital sign processing method including generating, by a pulse-wave sensor, a pulse-wave signal.

A heart-rate information item is output on the basis of the generated pulse-wave signal.

A first frequency band is set by a first filter unit on the basis of the output heart-rate information item, and The set first frequency band of the pulse-wave signal is allowed by the first filter unit to pass through the first filter unit.

According to still another embodiment of the present technology, there is provided an information processing device including an acquisition unit, an output unit, and a first filter unit.

The acquisition unit acquires a pulse-wave signal.

The output unit outputs a heart-rate information item on the basis of the acquired pulse-wave signal.

The first filter unit
sets a first frequency band on the basis of the output heart-rate information item, and
allows the set first frequency band of the pulse-wave signal to pass through the first filter unit.

Advantageous Effects of Invention

As described hereinabove, according to the present technology, highly accurate heart-rate measurement can be performed. Note that, the advantages disclosed herein are not necessarily limited to those described hereinabove, and all the advantages described hereinabove and hereinbelow can be obtained.

BRIEF DESCRIPTION OF DRAWINGS

FIG. 10 A table showing an example of data items stored in a second filter bank.

FIG. 15 A table showing an example of data items stored in a first filter bank.

MODE(S) FOR CARRYING OUT THE INVENTION

Now, embodiments according to the present technology are described with reference to the drawings.

First Embodiment

[Configuration of Heart-Rate Measurement Device]

Figure 1A:
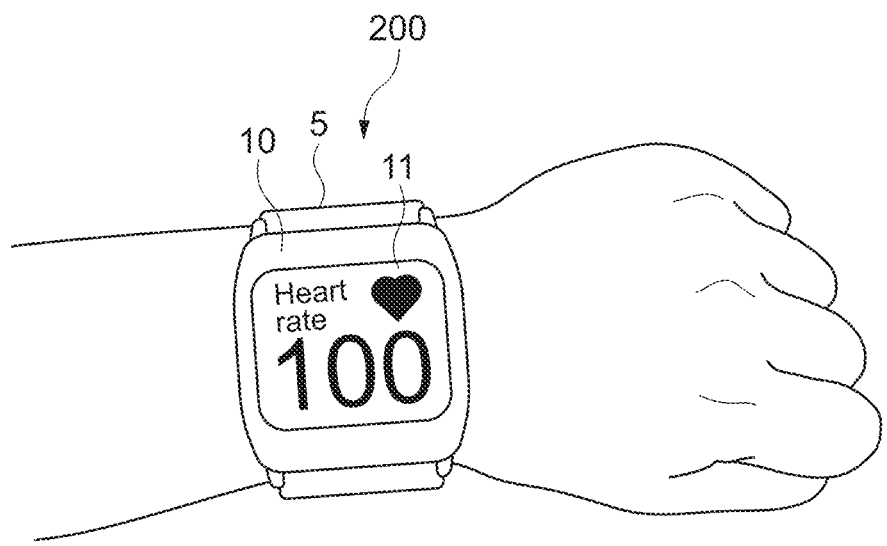
FIGS. 1A and 1B Schematic views illustrating a configuration example of a heart-rate measurement device according to an embodiment of the present technology.
Figure 1B:
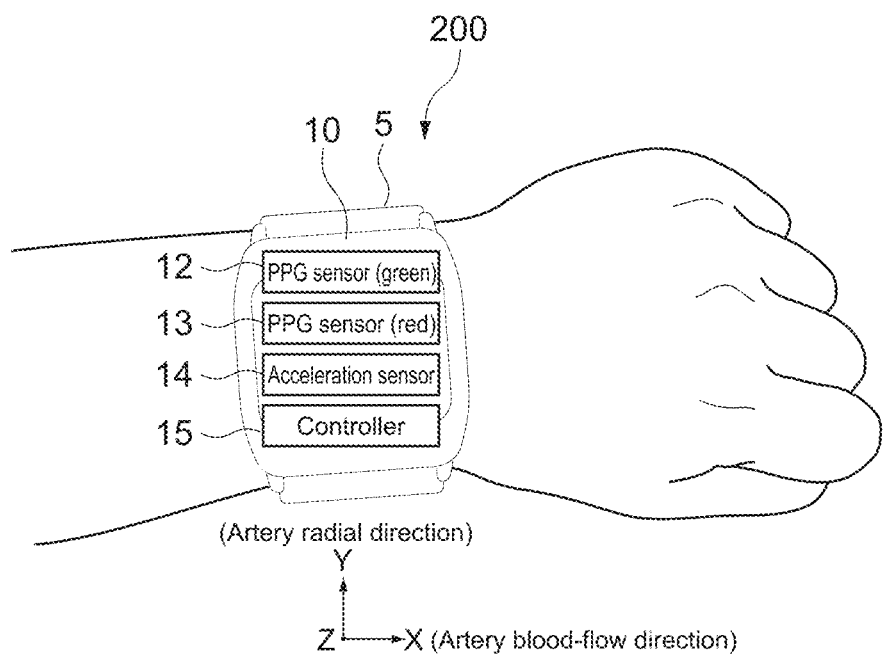

FIGS. 1A and 1B are schematic views illustrating a configuration example of a heart-rate measurement device according to an embodiment of the present technology. A heart-rate measurement device 200, which is a wristband-type PPG heart-rate sensor, is used by being worn on a wrist of a user. In this embodiment, the heart-rate measurement device 200 corresponds to a vital sign processing device.

In the PPG, pulse waves are measured from a volume fluctuation of a blood flow. In the PPG, light beams are radiated from a light emitting unit such as an LED (Light Emitting Diode) to skin. The radiated light beams are absorbed into, scattered by, or reflected by blood and subcutaneous tissue lying approximately several mm under the skin. An intensity of a light beam that has returned at this time from under the skin is measured by a light receiving unit such as a photodetector. In this way, blood-flow changes in capillaries distributed under the skin are measured.

As illustrated in FIGS. 1A and 1B, the heart-rate measurement device 200 includes a wearing band 5 and a sensor body portion 10. The wearing band 5 is connected to the sensor body portion 10, and is held in contact with the wrist of the user. The configuration of the wearing band 5 is not particularly limited.

The sensor body portion 10 includes a display unit 11 that displays a measured heart rate. The display unit 11 is a liquid-crystal or an EL (Electro-Luminescence) display device. The display unit 11 may have a touchscreen configuration such that operations by the user can be input thereto.

As schematically illustrated in FIG. 1B, the sensor body portion 10 includes a first PPG sensor 12, a second PPG sensor 13, an acceleration sensor 14, and a controller 15. The first PPG sensor 12 and the second PPG sensor 13 are provided on a side to be held in contact with the wrist of the user. The acceleration sensor 14 and the controller 15 are provided typically in the sensor body portion 10.

The first PPG sensor 12 includes a first light-emitting unit that emits, as light beams in a first wavelength band, green light beams in a green wavelength band (for example, from approximately 500 nm to approximately 570 nm) toward a measurement site, and a first light-receiving unit that detect light intensities of reflected light beams among the green light beams from under the skin at the measurement site (none of the units is shown). The first PPG sensor 12 is provided mainly for measuring the blood-flow changes.

The second PPG sensor 13 includes a second light-emitting unit that emits, as light beams in a second wavelength band, red light beams in a red wavelength band (for example, from approximately 620 nm to approximately 750 nm) toward the measurement site, and a second light-receiving unit that detect light intensities of reflected light beams among the red light beams from under the skin at the measurement site (none of the units is shown).

The red light beams with a long wavelength, which are emitted from the second PPG sensor 13, reach deep body tissue under the skin. Thus, feedback light beams of the red light beams emitted from the second PPG sensor are modulated by deformation of the body tissues due, for example, to movements of fingers and the wrist (movements of bones). Focusing on this characteristics, in this embodiment, the second PPG sensor 13 is provided mainly for generating reference signals that have high correlation with a noise generated by the movements of the fingers and the wrist.

In this embodiment, the first PPG sensor 12 and the second PPG sensor 13 constitute a pulse-wave sensor unit. The first PPG sensor 12, which functions as a pulse-wave-signal pulse-wave sensor, generates the pulse-wave signals. Further, the light beams in the first wavelength band, which are emitted from the first light-emitting unit, correspond to light beams in a predetermined wavelength band. The second PPG sensor 13 generates reference pulse-wave signals for generating the above-mentioned reference signals. Further, the pulse-wave signals and the reference pulse-wave signals correspond also to pulse-wave-candidate signals. The configurations of the first PPG sensor 12 and the second PPG sensor 13 are not particularly limited, and may be designed as appropriate.

The acceleration sensor 14 measures accelerations in three X-, Y-, and Z-axes at the measurement site on which the heart-rate measurement device 200 is worn. The acceleration sensor 14 is provided mainly for measuring a cyclic movement of an arm during walking, jogging, running, and the like. The acceleration sensor 14 functions as a body-motion sensor, and the accelerations to be measured in the three axes are output as body-motion signals. The configuration of the acceleration sensor 14 is not particularly limited. Further, as the body-motion sensor, for example, a three-axis gyroscopic sensor may be used instead of or in addition to the acceleration sensor 14.

As illustrated in FIG. 1B, in this embodiment, a right-and-left direction of the sensor body portion 10 is defined as the X-axis direction, and an upper-and-lower direction of the same is defined as the Y-axis direction. Further, another direction orthogonal to both the X-axis direction and the Y-axis direction (direction perpendicular to a surface of the sensor body portion 10) is defined as the Z-axis direction. Further, the X-axis direction is regarded as an artery blood-flow direction at the measurement site, and the Y-axis direction is regarded as an artery radial direction at the same. As a matter of course, directions are not necessarily limited to these directions.

The controller 15 controls operations of blocks in the heart-rate measurement device 200. The controller 15 has a hardware configuration necessary for a computer, specifically, includes a CPU and memories (RAM and ROM). When the CPU loads a program stored in the ROM or the like to the RAM, and then executes the program, various processes are executed. As the controller 15, there may be used, for example, PLDs (Programmable Logic Devices) such as an FPGA (Field Programmable Gate Array), or other devices such as an ASIC (Application Specific Integrated Circuit).

Figure 2:
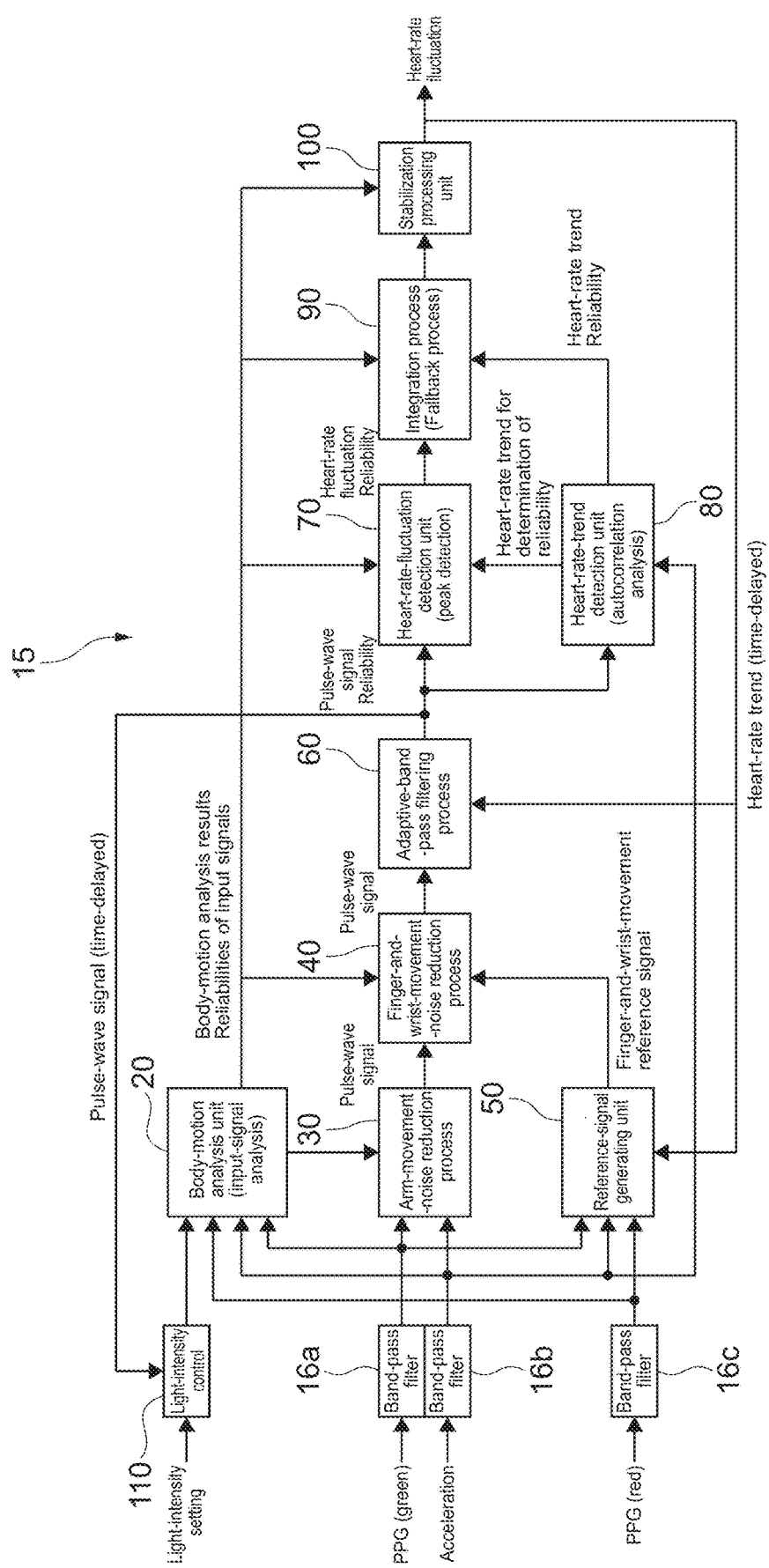
FIG. 2 A block diagram showing a functional configuration example of a controller.

In this embodiment, when the CPU of the controller 15 executes a program according to this embodiment, functions of blocks described hereinbelow with reference, for example, to FIG. 2 are exerted. By cooperation between these functional blocks and hardware modules such as the first PPG sensor 12, a vital sign processing method according to this embodiment is carried out. Specifically, on the basis of the pulse-wave signals that are output from the first PPG sensor 12, heart-rate information items of the user are generated. As a matter of course, in order to exert the functions of the blocks shown, for example, in FIG. 2, dedicated hardware modules such as an IC (integrated circuit) may be used.

FIG. 2 is a block diagram showing a functional configuration example of the controller 15. "PPG (green)," "Acceleration," and "PPG (red)" shown in FIG. 2 correspond respectively to the pulse-wave signal from the first PPG sensor 12, the body-motion signal from the acceleration sensor 14, and the reference pulse-wave signal from the second PPG sensor 13.

The controller 15 includes band-pass filters 16a to 16c, a body-motion analysis unit 20, a first noise-reduction processing unit 30, a second noise-reduction processing unit 40, a reference-signal generating unit 50, an adaptive-band-pass-filter processing unit 60, a heart-rate-fluctuation detection unit 70, a heart-rate-trend detection unit 80, an integration processing unit 90, a stabilization processing unit 100, and a light-intensity control unit 110. As described hereinbelow, by the operations of the blocks, the heart rate is output as the heart-rate information item.

[Operation of Heart-Rate Measurement Device]

Figure 3:
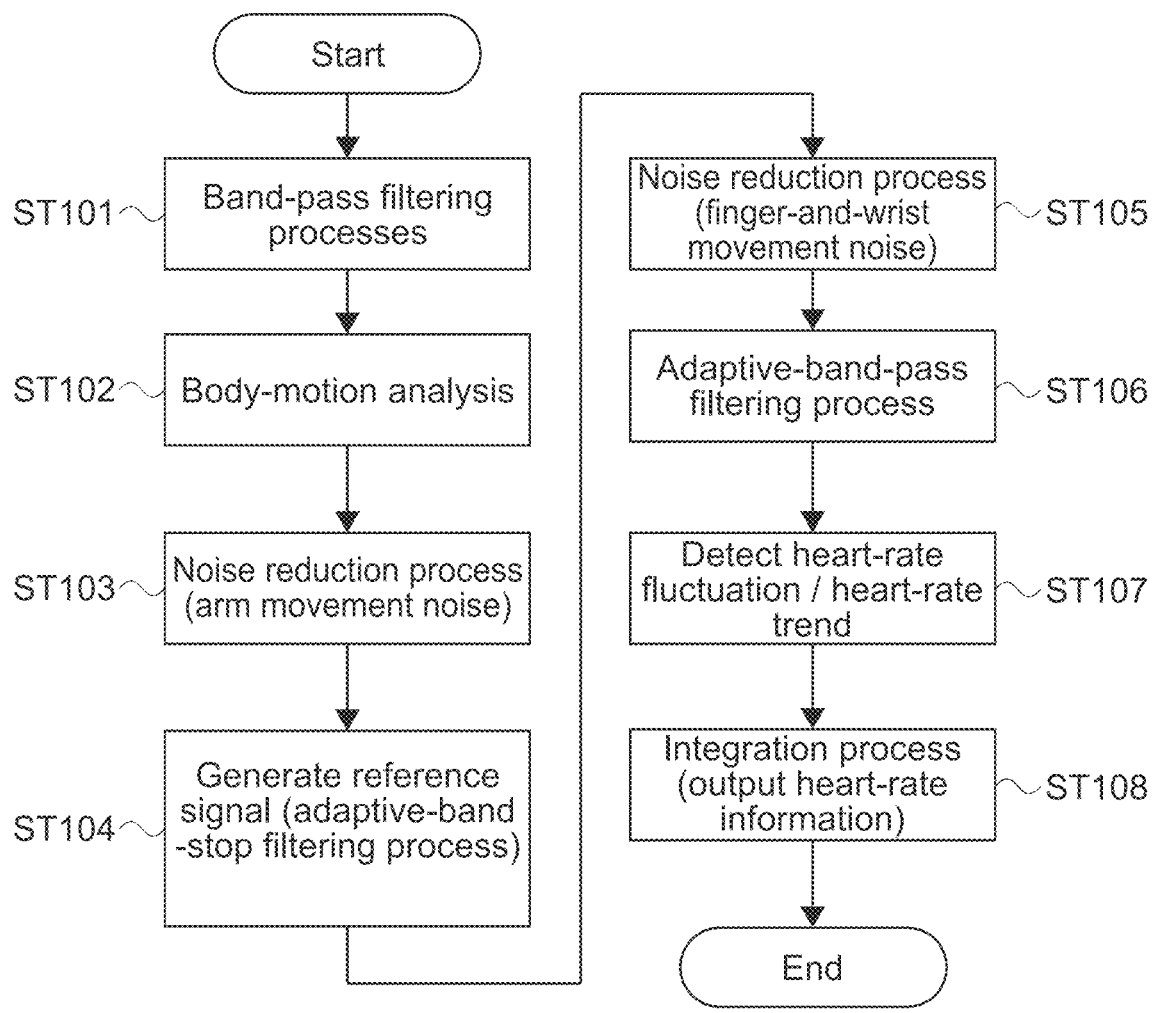
FIG. 3 A flowchart showing an example of outputting a heart-rate information item.

FIG. 3 is a flowchart showing an example of outputting the heart-rate information item. First, the band-pass filters 16a to 16c execute band-pass filtering processes (Step 101). The band-pass filters 16a to 16c extract fluctuation components associated with pulsations and the deformation of the body tissues from the output signals from the PPG sensors. Further, the band-pass filter 16b removes offset and an electrical noise that are caused by gravitational acceleration.

Figure 4:
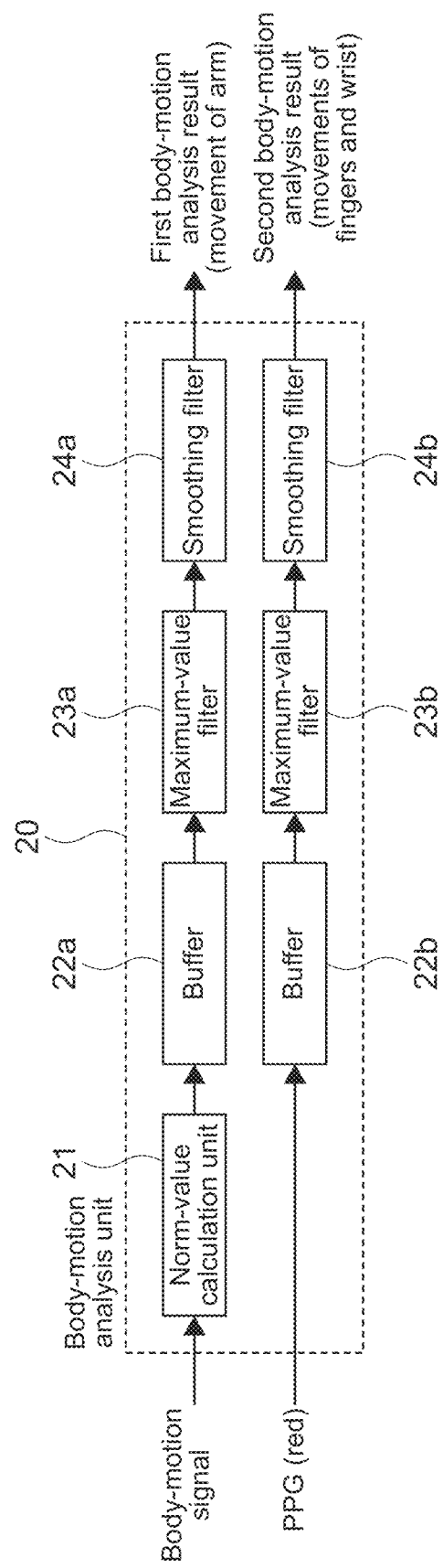
FIG. 4 An explanatory diagram showing a concept of a body-motion analysis by a body-motion analysis unit.
Figure 5:
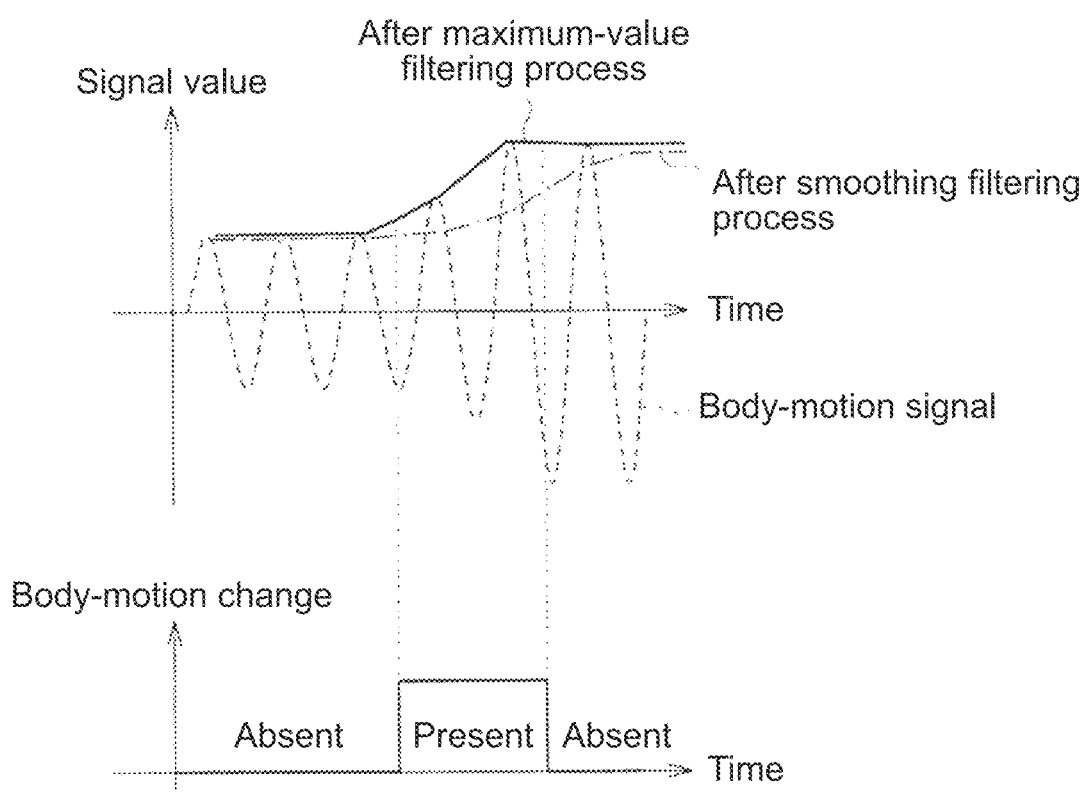
FIG. 5 An explanatory graph showing the concept of the body-motion analysis by the body-motion analysis unit.

The body-motion analysis unit 20 analyzes a body-motion intensity at the measurement site (Step 102). FIG. 4 and FIG. 5 are respectively an explanatory diagram and an explanatory graph showing a concept of the body-motion analysis by the body-motion analysis unit 20.

The body-motion analysis unit 20 includes a norm-value calculation unit 21, buffers 22a and 22b, maximum-value filters 23a and 23b, and smoothing filters 24a and 24b. When the acceleration sensor 14 is a three-axis acceleration sensor, the norm-value calculation unit 21 calculates an acceleration norm from a three-axis acceleration signal being the body-motion signal. The acceleration norm is output to the maximum-value filter 23a via the buffer 22a, and subjected to a maximum-value filtering process. The body-motion signal (norm value) that has been subjected to the maximum-value filtering process is output to the smoothing filter 24a, and subjected to a smoothing filtering process. By executing a threshold process on a difference between the body-motion signal that has been subjected to the maximum-value filtering process and the body-motion signal that has been subjected to the smoothing filtering process, the body-motion intensity at the measurement site and a body-motion change in response to a change of a body-motion frequency can be detected.

In the upper part of FIG. 5, the ordinate axis represents signal values, and the abscissa axis represents time. In the lower part of FIG. 5, the ordinate axis represents status of the body-motion change (presence/absence of the body-motion change), and the abscissa axis represents the time. The upper part of FIG. 5 shows the body-motion signal before the filtering processes, the body-motion signal after the smoothing filtering process, and the body-motion signal after the maximum-value filtering process. For example, from the body-motion signal after the smoothing filtering process and the body-motion signal after the maximum-value filtering process as shown in the upper part of FIG. 5, presence/absence of the body-motion change (mainly, movements of the arm) can be detected as shown in the lower part of FIG. 5.

Similarly, with regard to the reference pulse-wave signal that is output from the second PPG sensor 13, on the basis of outputs from the maximum-value filter 23b and the smoothing filter 24b, presence/absence of the body-motion change (mainly, movements of the fingers and the wrist) can be detected. Hereinbelow, the word "mainly" may be omitted.

In this way, the body-motion analysis unit 20 outputs a first body-motion analysis result about the cyclic movement of the arm, and a second body-motion analysis result about non-cyclic movements of the fingers and the wrist. Note that, as examples of the smoothing filters to be used, there may be mentioned an FIR (Finite Impulse Response) filter and an IIR (Infinite Impulse Response) filter.

Further, in this embodiment, the body-motion analysis unit 20 calculates reliabilities of the pulse-wave signal and the reference pulse-wave signal. These reliabilities are calculated on the basis of setting values of light intensities of the first PPG sensor 12 and the second PPG sensor 13, the setting values being set by the light-intensity control unit 110. For example, when the light intensities of the light-emitting units are each less than a predetermined threshold, or when the setting values of the light intensities have changed, the reliabilities of the pulse-wave signal and the reference pulse-wave signal decrease. The method of calculating the reliabilities is not limited, and other methods may be employed.

The first noise-reduction processing unit 30 executes a process of reducing a body-motion noise that is caused by the movement of the arm (hereinafter, abridged as "arm movement noise") (Step 103). Note that, in FIG. 2, the first noise-reduction processing unit 30 is expressed as an arm-movement-noise-reduction processing unit 30.

Figure 6:
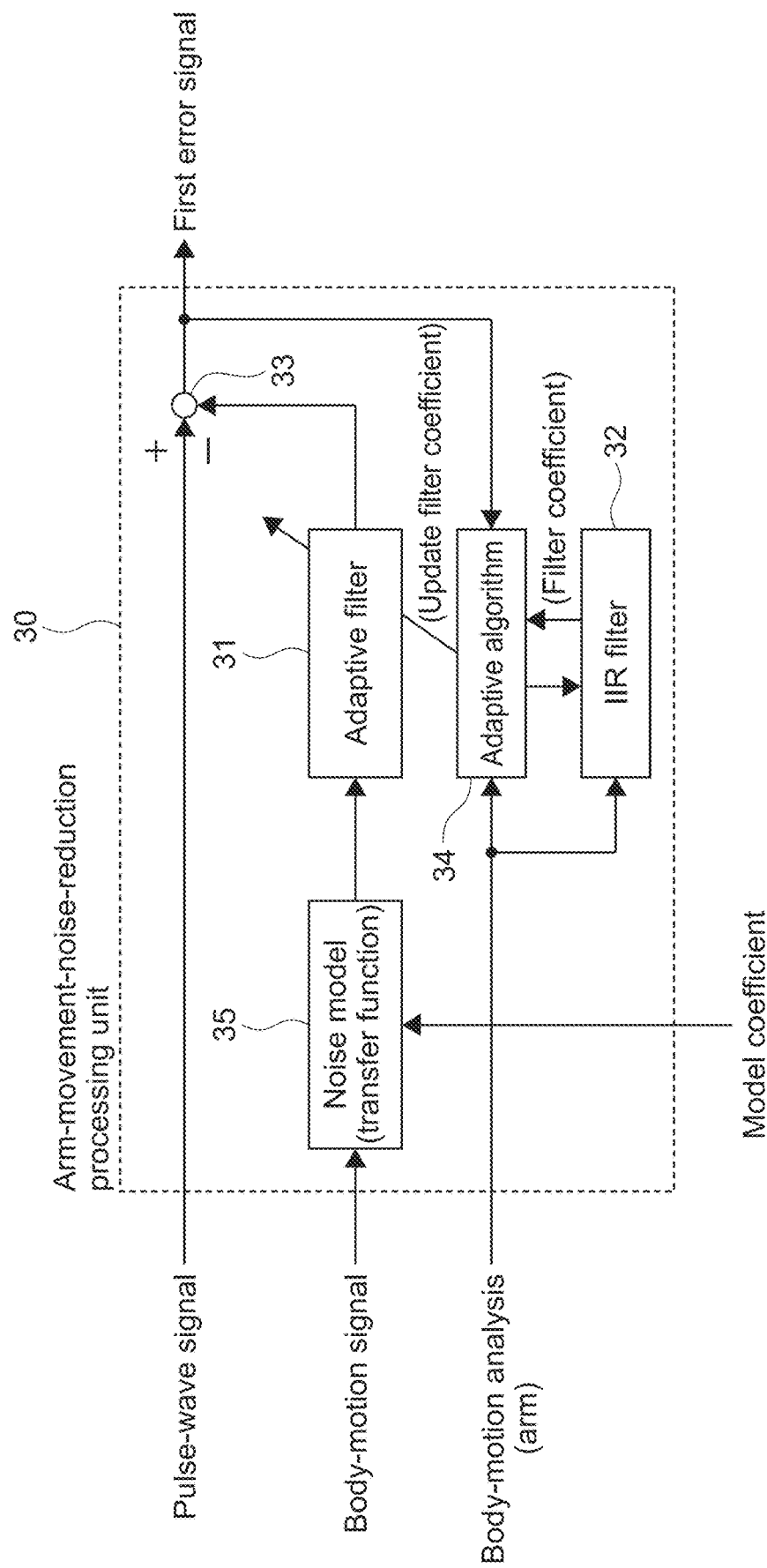
FIG. 6 A block diagram showing a configuration example of a first noise-reduction processing unit.

FIG. 6 is a block diagram showing a configuration example of the first noise-reduction processing unit 30. The first noise-reduction processing unit 30 includes an adaptive filter 31 (first adaptive filter), an IIR filter 32, and a subtractor 33. An input signal to the adaptive filter 31 is the body-motion signal, and a monitoring signal is the pulse-wave signal that is output from the first PPG sensor 12. The subtractor 33 subtracts an output value of the adaptive filter 31 from the pulse-wave signal, and then a first error signal is output. The first error signal corresponds to a pulse-wave signal from which the body-motion noise (arm movement noise) has been separated.

An adaptive-filter coefficient of the adaptive filter 31 is updated on the basis of the first body-motion analysis result by an adaptive algorithm 34 and the IIR filter 32. For example, when the adaptive algorithm 34 is an NLMS algorithm, a parameter for determining an update amount of the adaptive-filter coefficient, which is called a "step size," is controlled on the basis of the first body-motion analysis result. With this, a convergence time period in which an optimum coefficient is calculated is improved, and hence it is possible to follow the change of the body-motion frequency.

Further, in order that the body-motion noise (false signal) contained in the monitoring signal is separated by the adaptive filter 31, it is preferred that the input signal and the body-motion noise have high correlation with each other. In this embodiment, as shown in FIG. 6, influence of the body motion on the blood flow is modeled as a noise model 35, and a transfer function (FIR filter coefficient) from the body motion to the blood flow is calculated and recorded in advance. A result of the FIR filtering process on the body-motion signal is input to the adaptive filter 31. In other words, the body-motion signal is not utilized as it is as the input signal, and the result of the FIR filtering process is utilized as the input signal. As a result, the convergence time period in which the optimum coefficient at the times when the body-motion intensity and the body-motion frequency have changed is calculated is shortened.

The transfer function of the noise model 35 depends, for example, on conditions of blood vessels and the blood flow, and hence the optimum coefficient is different from user to user. Thus, in this embodiment, at the time when the user uses the heart-rate measurement device 200, a procedure of calculating the transfer function from the body motion to the blood flow as the noise model 35 is executed.

Figure 7:
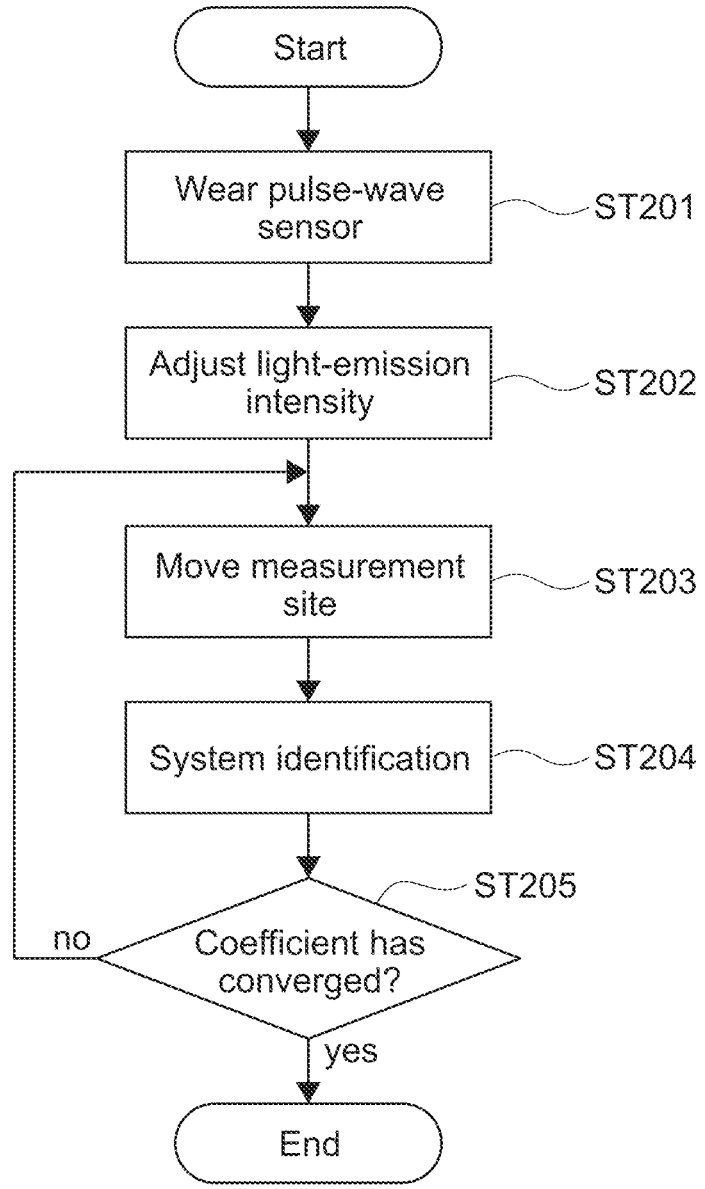
FIG. 7 A flowchart showing a calculation example of a transfer function.

FIG. 7 is a flowchart showing a calculation example of the transfer function. First, the first PPG sensor 12 is worn on the measurement site (Step 201). A feedback light intensity is different from person to person depending, for example, on skin colors at the measurement site. Thus, in order that the pulse-wave signal is not saturated in a resting state, the light intensity of the first light-emitting unit of the first PPG sensor 12 is controlled (Step 202).

The user is prompted to move the measurement site. Specifically, impulsive body motions in the artery blood-flow direction are applied to the measurement site (refer to FIG. 1B), and then the pulse-wave signal and the body-motion signal are measured (Step 203). The first noise-reduction processing unit 30, specifically, the adaptive filter 31 therein performs system identification (Step 204), with the body-motion signal generated by the impulsive body motions being input as the input signal, and the pulse-wave signal being output as the output signal.

Whether or not the transfer function (FIR filter coefficient) has converged is determined (Step 205). When the transfer function has not converged (No in Step 205), the procedure returns to Step 203. When the transfer function has converged (Yes in Step 205), the procedure is ended.

Note that, although the transfer function (FIR filter coefficient) from the body motion to the blood flow is exemplified as the noise model 35 in the above description, as another embodiment, approximation by N-th order polynomial may be employed. Specifically, a coefficient of the N-th order polynomial may be calculated by a least squares method.

Further, the calculated adaptive-filter coefficient is subjected to an IIR filtering process by the IIR filter 32. For example, on a premise that a previous value of one sample before is 0 (zero), when a determination that the user is in the resting state is made, the IIR filtering process is executed, and the adaptive filtering process is not executed. During an exercise, by setting a feedback factor to 0.0 so as not to execute the IIR filtering process, the adaptive filtering process is executed. With this configuration, merely by controlling the feedback factor of the IIR filter 32 in accordance with the first body-motion analysis result, whether or not to execute the adaptive filtering process can be smoothly switched.

By the above-described devising, even when the body-motion intensity and the body-motion frequency abruptly change, the convergence time period of the adaptive filtering process is improved. Thus, an advantage of reducing noises can be sufficiently obtained.

Figure 8:
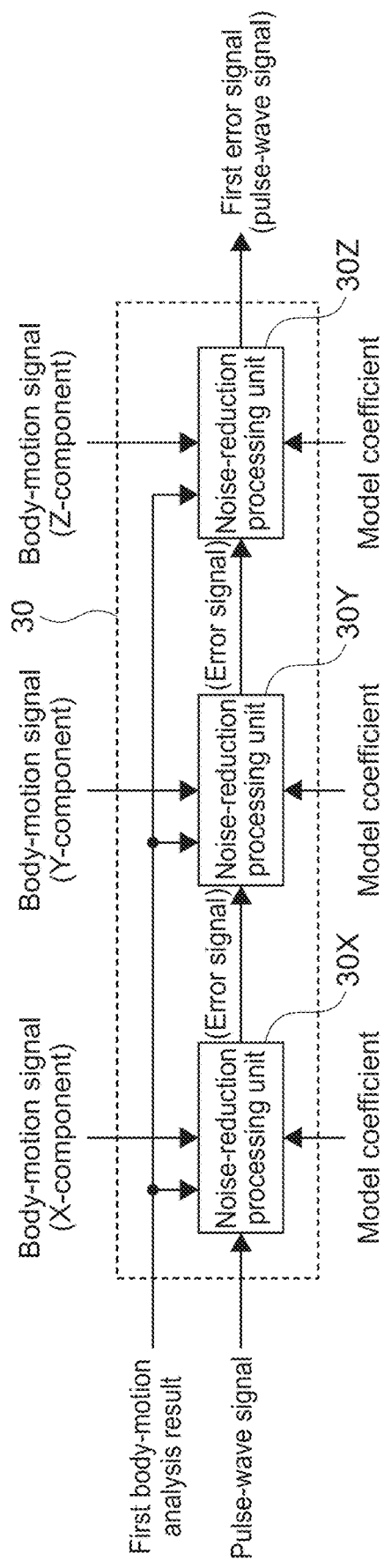
FIG. 8 A block diagram showing a configuration example of the first noise-reduction processing unit at a time when an acceleration sensor is a three-axis acceleration sensor.

FIG. 8 is a block diagram showing a configuration example of the first noise-reduction processing unit 30 at the time when the acceleration sensor 14 is the three-axis acceleration sensor. There is no particular limitation on this configuration as long as transfer functions from components of the three-axis accelerations to the blood flow are calculated in advance, and as long as noise-reduction processing units 30X, 30Y, and 30Z corresponding to the X-, the Y-, and the Z-acceleration components are cascaded.

For example, a model coefficient, an X-component of the body-motion signal, the first body-motion analysis result, and the pulse-wave signal before the noise reduction process are input to the noise-reduction processing unit 30X. A model coefficient, a Y-component of the body-motion signal, the first body-motion analysis result, and an output (error signal) from the noise-reduction processing unit 30X are input to the noise-reduction processing unit 30Y. A model coefficient, a Z-component of the body-motion signal, the first body-motion analysis result, and an output (error signal) from the noise-reduction processing unit 30Y are input to the noise-reduction processing unit 30Z. An output (error signal) from the noise-reduction processing unit 30Z is the first error signal.

As shown in FIG. 2, in this embodiment, not only the first error signal, but also its reliability is calculated. For example, by analyzing a temporal change of the adaptive-filter coefficient, whether or not the arm-movement-noise reduction process is properly executed is analyzed. With this, the reliability of the first error signal to be output is output as a parameter. Specifically, under a state in which a sum of absolute values of time differences between filter coefficients has been calculated, when the coefficient abruptly changes or is equal to or higher than a threshold, it is determined that the reliability is low or there is no reliability. The method of calculating the reliability is not limited, and other methods may be employed. Alternatively, a reliability based on the light intensity of the first PPG sensor 12, which is output from the body-motion analysis unit 20, may be utilized as appropriate.

The reference-signal generating unit 50 shown in FIG. 2 generates a reference signal (Step 104). The reference signal is a signal to be used for separating a body-motion noise that is caused by the movements of the fingers and the wrist (hereinafter, abridged as "finger-and-wrist movement noise").

Figure 9:
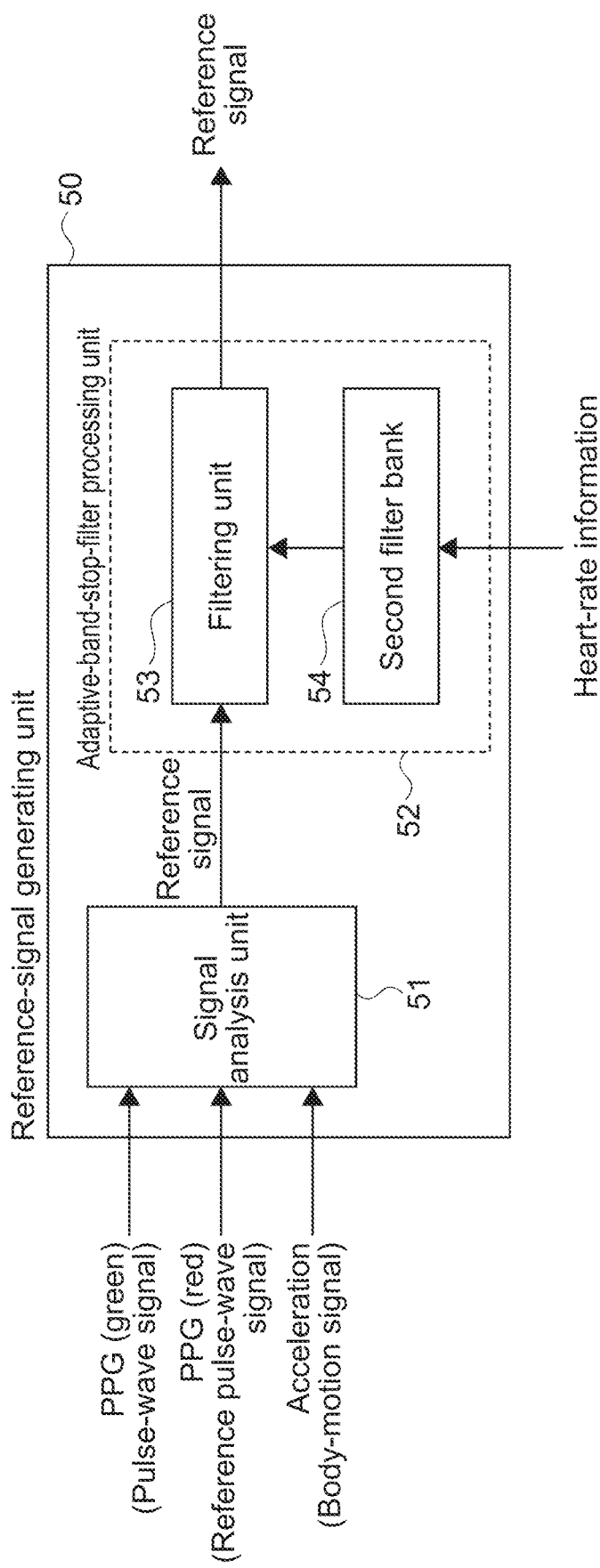
FIG. 9 A block diagram showing a configuration example of a reference-signal generating unit.

FIG. 9 is a block diagram showing a configuration example of the reference-signal generating unit. The reference-signal generating unit 50 includes a signal analysis unit 51 and an adaptive-band-elimination-filter processing unit 52. The reference signal generated by the signal analysis unit 51 is filtered by the adaptive-band-elimination-filter processing unit 52. In this embodiment, the reference-signal generating unit 50 corresponds to a generating unit, and the adaptive-band-elimination-filter processing unit 52 corresponds to a second filter unit.

It is preferred that the reference signal have high correlation with the finger-and-wrist movement noise. In this embodiment, the reference signal is generated on the basis of the pulse-wave signal from the first PPG sensor 12, the reference pulse-wave signal from the second PPG sensor 13, and the body-motion signal from the acceleration sensor 14.

The signal analysis unit 51 performs, for example, main-component analysis of both the pulse-wave signal and the reference pulse-wave signal, and a noise signal is selected from generated two signals. In the PPG, intensities of body-motion noise components are higher than those of the signal components, and hence one of the signals subjected to the separation, which has higher power than another, is a signal having high correlation with the finger-and-wrist movement noise. This signal is used as the reference signal. The method of generating the reference signal is not limited. For example, a signal generated by combining the pulse-wave signal and the reference pulse-wave signal, or a signal based only on the reference pulse-wave signal may be used as the reference signal. Alternatively, the pulse-wave reference signal itself may be used as the reference signal. Still alternatively, the body-motion signal output from the acceleration sensor 14 may be used as the reference signal.

An adaptive-band-elimination filtering process is executed on the reference signal generated by the signal analysis unit 51. As shown in FIG. 9, the adaptive-band-elimination-filter processing unit 52 includes a filtering unit 53 and a second filter bank 54, and the heart-rate information item to be output from the stabilization processing unit 100 is input thereto. Details of the stabilization processing unit 100 and the heart-rate information item are described below. The filtering unit 53 functions as a band-elimination filter. The second filter bank 54 includes a plurality of band-elimination filters as filter coefficients corresponding respectively to filters.

FIG. 10 is a table showing an example of data items stored in the second filter bank 54. The second filter bank 54 stores, in correlation with each other, filter IDs (1, 2, . . . , N) of the band-elimination filters, heart-rate ranges, and the filter coefficients. In the example shown in FIG. 10, the filter coefficients of the "N" types corresponding to heart rates of from 40 bpm to 200 bpm are shown.

For example, in a row of the filter ID of 2, a conditional expression at a time when a heart rate (hr) is 55 bpm or more and less than 65 bpm (55 bpm≤hr<65 bpm) is stored as the heart-rate range. Further, a data item "BScoef_vector2" is stored as the filter coefficient.

Figures 11A, 11B:
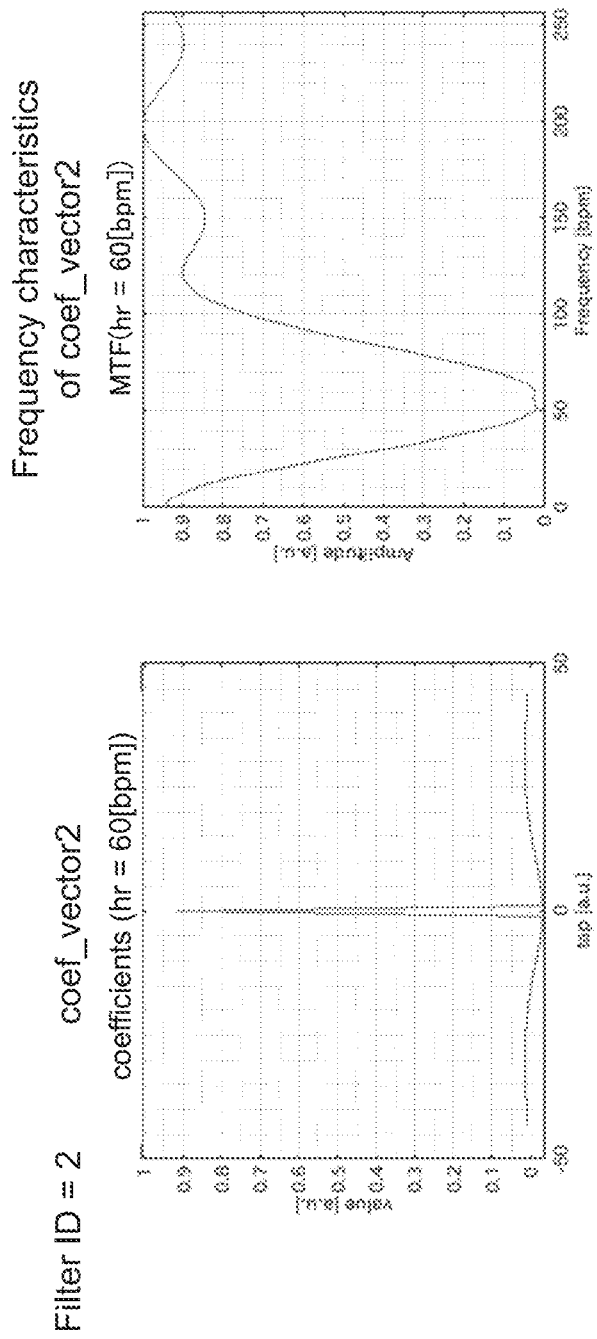
FIGS. 11A and 11B Graphs showing an example of band-elimination filters.

FIGS. 11A and 11B include graphs showing an example of the band-elimination filters. FIG. 11A is a graph showing the filter coefficient (BScoef_vector2) at the time when the filter ID is 2. The abscissa axis and the ordinate axis in FIG. 11A respectively represent the numbers of taps and the filter coefficients. With use of the filter coefficients shown in FIG. 11A, the band-elimination filter (digital filter) is set.

FIG. 11B is a graph showing frequency characteristics of the band-elimination filter that uses the filter coefficient corresponding to the filtering ID of 2. The abscissa axis in FIG. 11B represents frequencies, and the ordinate axis in the same represents intensities (transmission rates) of a signal, which pass through the band-elimination filter. The graph of FIG. 11B shows a largest valley pattern with a center frequency of approximately 55 bpm (hereinafter, simplified as "valley pattern"). For example, intensities of frequency components at frequencies of from 50 bpm to 60 bpm are attenuated by 95% or more. Meanwhile, for example, intensities of frequency components at frequencies exceeding 110 bpm are attenuated by approximately 15% at most.

As shown in FIG. 11B, the band-elimination filter attenuates the intensities of the frequency components in the particular frequency band, and allows the frequency components in the other band-eliminationass therethrough. In this embodiment, a frequency band in which the intensities of the frequency components are reduced to half or less is defined as a frequency band of each of the band-elimination filters (stop bands). In other words, frequencies each having an attenuation amount of 50% respectively on a high frequency side and a low frequency side of the valley pattern are respectively an upper-limit frequency Fmax and a lower-limit frequency Fmin of each of the stop bands. Thus, a frequency F within the stop band is expressed by Fmin≤F≤Fmax, and a bandwidth ΔF of the stop band corresponds to a half width of the valley pattern (ΔF=Fmax−Fmin). Specifically, in the example shown in FIG. 11B, Fmax, Fmin, and ΔF are set respectively to 88 bpm, 26 bpm, and 62 bpm.

The frequency characteristics of the band-elimination filters, such as the stop bands, are set as appropriate for removing a heart-rate component from the reference signal. Typically, the band-elimination filters are set with reference to the heart-rate ranges shown in FIG. 10. In addition, the filter coefficients may be calculated such that the set stop bands exert their functions. In this embodiment, the stop bands are set to include the heart-rate ranges shown in FIG. 10. For example, the heart-rate ranges and the stop bands may match each other. The setting of the frequency characteristics of the band-elimination filters is not limited thereto, and these frequency characteristics may be set as appropriate. Alternatively, a profile of the valley pattern may be set as appropriate in accordance with the stop bands.

In this way, the band-elimination filters corresponding respectively to the heart-rate ranges can be selected from the plurality of filter coefficients stored in the second filter bank 54. Further, the stop bands of the band-elimination filters, for example, are appropriately set in accordance with corresponding ones of the heart-rate ranges. With this, filtering can be properly performed in the respective heart-rate ranges, and hence the heart-rate component can be properly removed from the reference signal. Note that, the information items to be stored in the second filter bank 54, for example, are not limited, and the half width of the valley pattern, for example, may be stored in advance.

Figure 12:
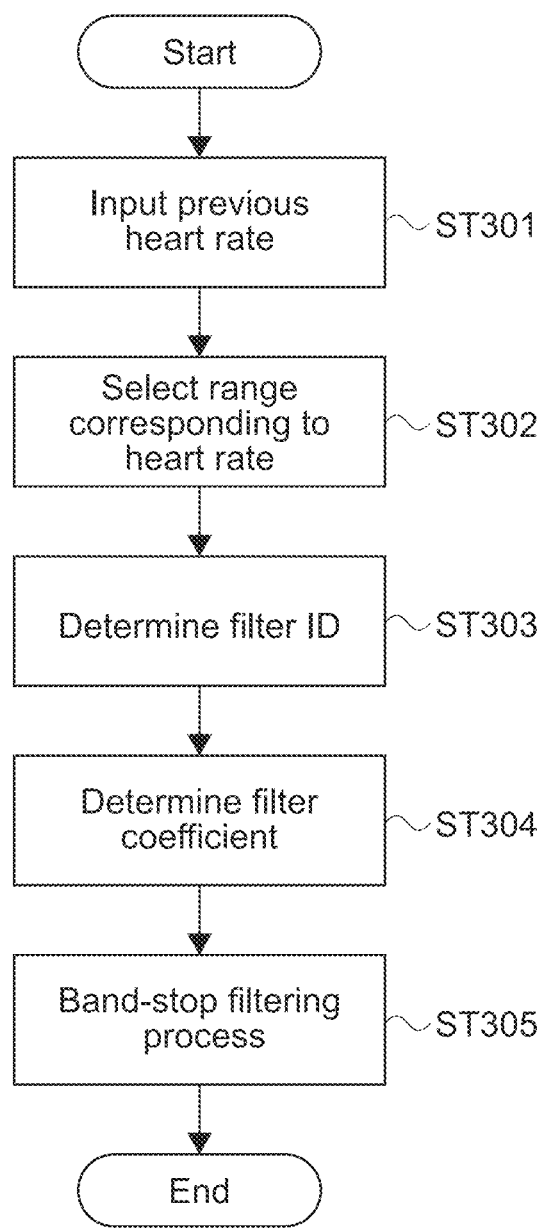
FIG. 12 A flowchart showing an example of a band-elimination filtering procedure.

FIG. 12 is a flowchart showing an example of a band-elimination filtering procedure. First, the heart rate included in the heart-rate information item is input to the adaptive-band-elimination-filter processing unit 52 (Step 301). This heart rate is a heart rate output (previously) from the stabilization processing unit 100 immediately before execution of the filtering procedure (hereinafter, abridged as "reference heart rate").

A range corresponding to the reference heart rate is selected from the second filter bank 54 (Step 302), and corresponding one of the filter IDs are determined (Step 303). For example, when the reference heart rate is 60 bpm, it is determined that the reference heart rate falls within the range of 55 bpm or more and less than 65 bpm, and "ID=2" is determined as the filter ID.

The filter coefficient is determined from the filter ID (Step 304). For example, when "ID=2" is determined, the filter coefficient is "BScoef_vector2" (refer to FIG. 10). The determined filter coefficient (hereinafter, described as "corresponding filter coefficient") is set as a filter coefficient of the filtering unit 53. In this way, the band-elimination filter that removes the frequency band including the reference heart rate is set in the filtering unit 53. In this embodiment, the stop band of the corresponding filter coefficient corresponds to a second frequency band.

In this embodiment, the adaptive-band-elimination-filter processing unit 52 selects the corresponding filter coefficient corresponding to the reference heart rate. Then, the stop band of the corresponding filter coefficient is set as a frequency band of the filtering unit. In other words, the adaptive-band-elimination-filter processing unit sets the stop band on the basis of the heart-rate information item.

The filtering unit 53 executes the band-elimination filtering process on the reference signal (Step 305). Of the frequency components contained in the reference signal, the frequency component within the stop band is removed. In other words, in accordance with the immediately-preceding heart rate (reference heart rate), the surrounding band components including the heart-rate component are removed, and the other bands are allowed to pass. Thus, a non-heart-rate component has been contained in the filtered reference signal, and the heart-rate component has been removed therefrom.

Referring back to FIG. 3, the second noise-reduction processing unit 40 executes a process of reducing the finger-and-wrist movement noise (Step 105). Note that, in FIG. 2, the second noise-reduction processing unit 40 is expressed as a finger-and-wrist-movement-noise-reduction processing unit 40.

Figure 13:
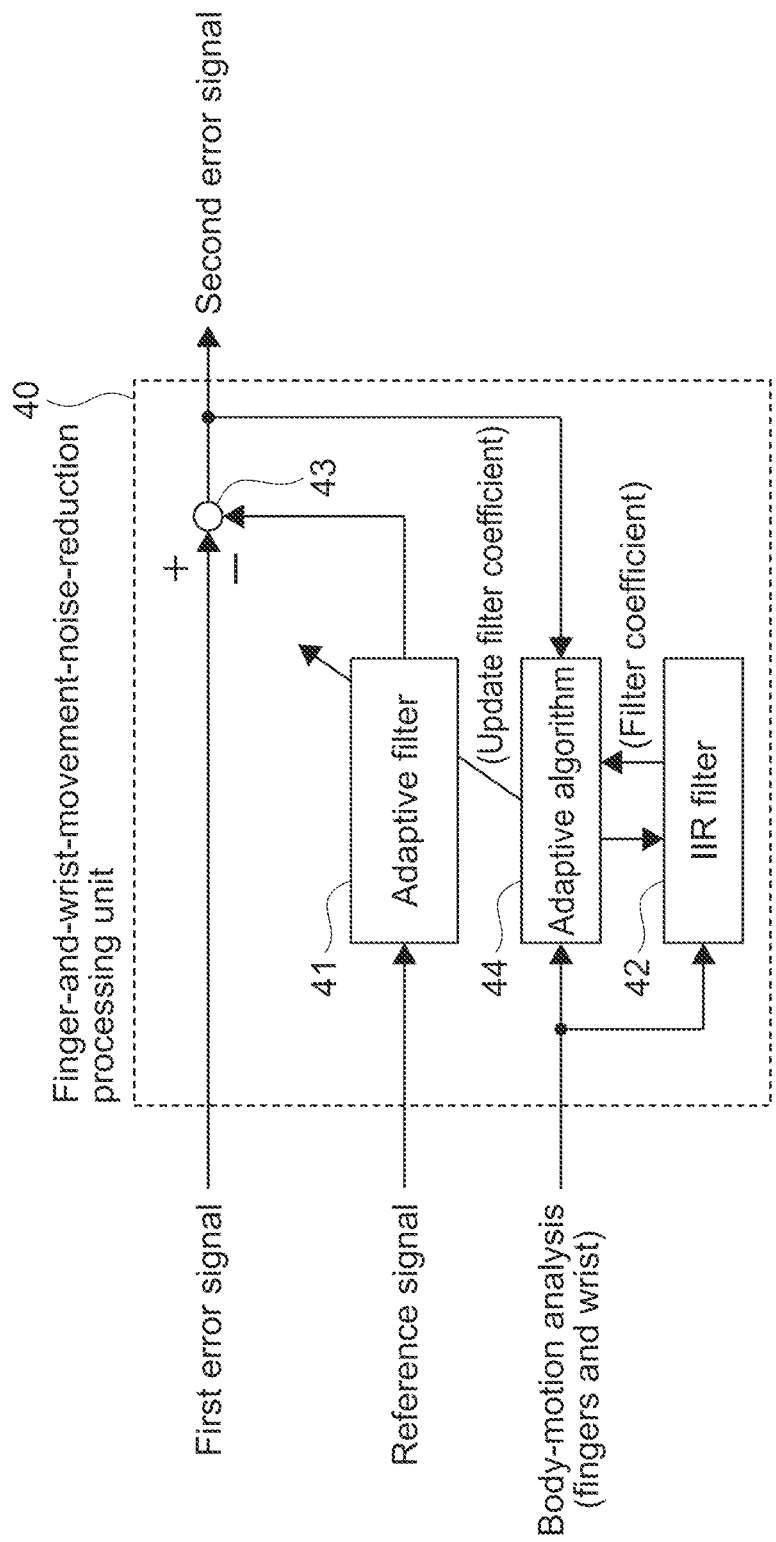
FIG. 13 A block diagram showing a configuration example of a second noise-reduction processing unit.

FIG. 13 is a block diagram showing a configuration example of the second noise-reduction processing unit 40. The second noise-reduction processing unit 40 includes an adaptive filter 41 (second adaptive filter), an IIR filter 42, and a subtractor 43. An input signal to the adaptive filter 41 is the reference signal, and a monitoring signal is the first error signal (pulse-wave signal) that is output from the first noise-reduction processing unit 30. The subtractor 43 subtracts an output value of the adaptive filter 41 from the first error signal, and then a second error signal is output. The second error signal corresponds to a pulse-wave signal from which the body-motion noise (finger-and-wrist movement noise) has been separated.

An adaptive-filter coefficient of the adaptive filter 41 is updated on the basis of the second body-motion analysis result by an adaptive algorithm 44 and the IIR filter 42. With this, a convergence time period in which an optimum coefficient is calculated is shortened, and hence it is possible to follow the change of the body-motion frequency.

Further, as in the first noise-reduction processing unit 30, the calculated adaptive-filter coefficient is subjected to an IIR filtering process by the IIR filter 42. Thus, merely by controlling a feedback factor of the IIR filter 42 in accordance with the second body-motion analysis result, whether or not to execute the adaptive filtering process can be smoothly switched.

Not only the second error signal, but also its reliability is calculated. For example, by analyzing a temporal change of the adaptive-filter coefficient, whether or not the arm-movement-noise reduction process is properly executed is analyzed. With this, the reliability of the second error signal to be output is output as a parameter. Specifically, under a state in which a sum of absolute values of time subtractions of filter coefficients has been calculated, when the coefficient abruptly changes or is equal to or higher than a threshold, it is determined that the reliability is low or there is no reliability. The method of calculating the reliability is not limited, and other methods may be employed. Alternatively, a reliability based on the light intensity of the second PPG sensor 13, which is output from the body-motion analysis unit 20, may be utilized as appropriate.

The adaptive-band-pass-filter processing unit 60 shown in FIG. 2 performs filtering on the basis of the heart rate (Step 106). The second error signal (pulse-wave signal) and the heart-rate information item that is output from the stabilization processing unit 100 are input to the adaptive-band-pass-filter processing unit 60.

Figure 14:
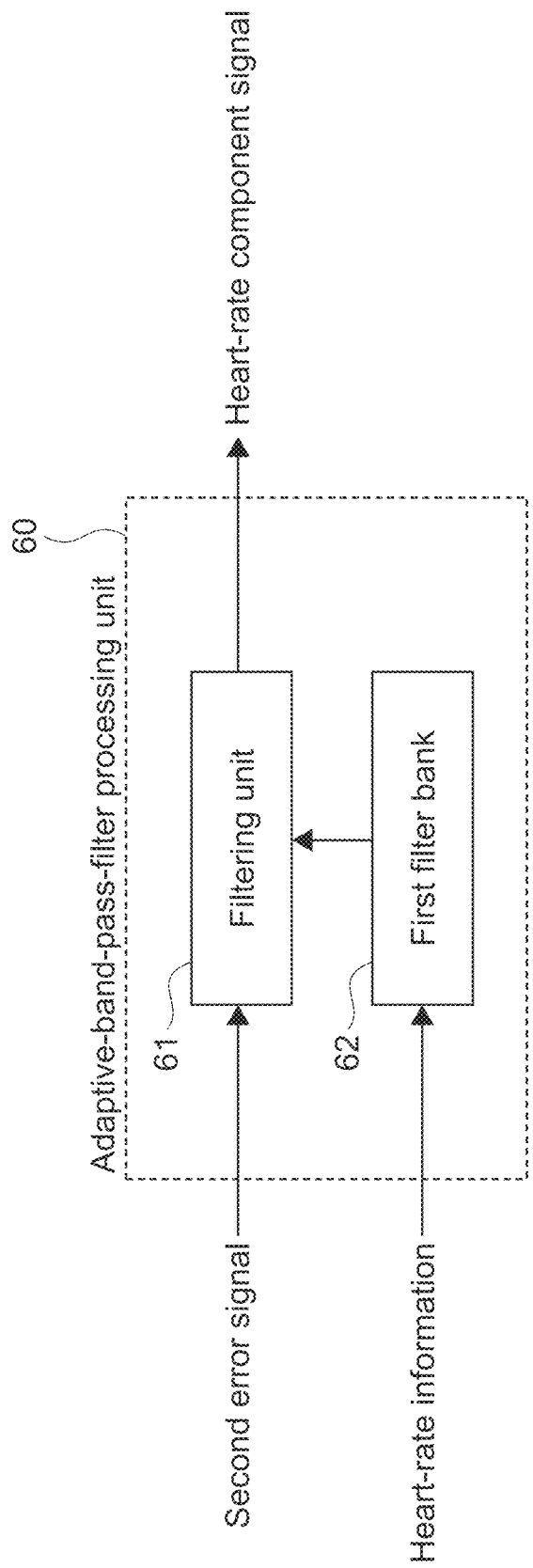
FIG. 14 A block diagram showing a configuration example of an adaptive-band-pass-filter processing unit.

FIG. 14 is a block diagram showing a configuration example of the adaptive-band-pass-filter processing unit. The adaptive-band-pass-filter processing unit 60 includes a filtering unit 61 and a first filter bank 62. The filtering unit 61 functions as a band-pass filter. In this embodiment, the filtering unit 61 filters the second error signal to output a heart-rate component signal. The first filter bank 62 includes a plurality of band-pass filters as filter coefficients corresponding respectively to filters.

FIG. 15 is a table showing an example of data items stored in the first filter bank. The first filter bank stores, in correlation with each other, filter IDs (1, 2, . . . , N) of the band-pass filters, the heart-rate ranges, and the filter coefficients. In the example shown in FIG. 15, the filter coefficients of the "N" types corresponding to the heart rates of from 40 bpm to 200 bpm are shown.

For example, in the row of the filter ID of 2, the conditional expression at the time when the heart rate (hr) is 55 bpm or more and less than 65 bpm (55 bpm≤hr<65 bpm) is stored as the heart-rate range. Further, a data item "BPcoef_vector2" is stored as the filter coefficient.

Figure 16:
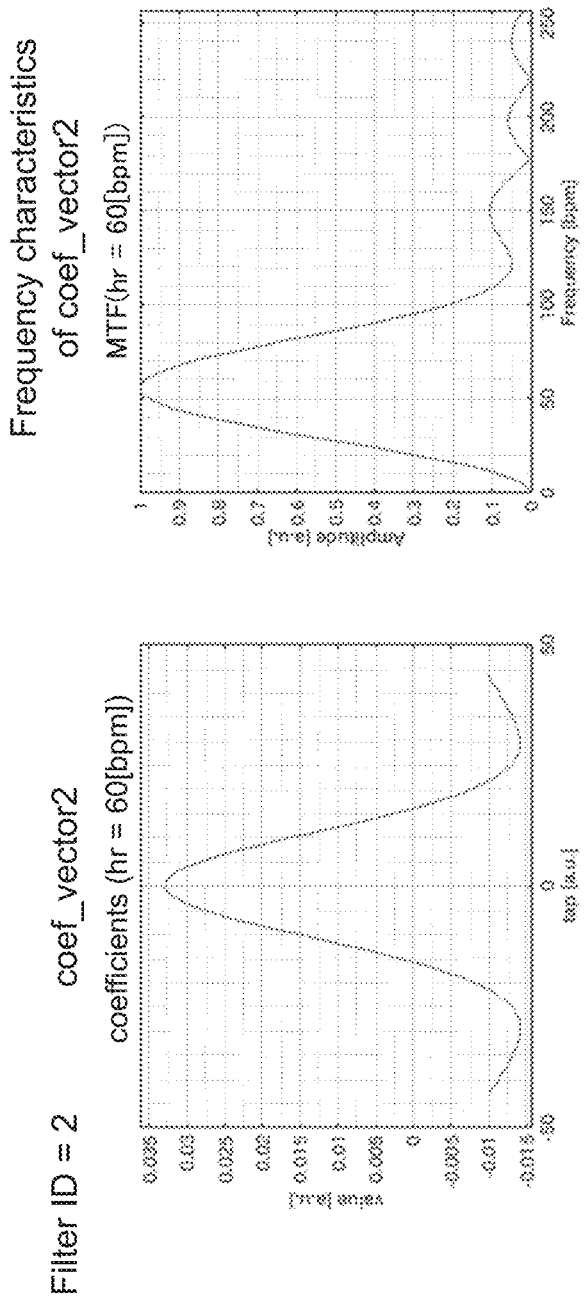
FIGS. 16A and 16B Graphs showing an example of band-pass filters.

FIGS. 16A and 16B include graphs showing an example of the band-pass filters. FIG. 16A is a graph showing the filter coefficient (BPcoef_vector2) at the time when the filter ID is 2. The abscissa axis and the ordinate axis in FIG. 16A respectively represent the numbers of taps and the filter coefficients. With use of the filter coefficients shown in FIG. 16A, the band-pass filter is set.

FIG. 16B is a graph showing frequency characteristics of the band-pass filter that uses the filter coefficient corresponding to the filtering ID of 2. The abscissa axis in FIG. 16B represents frequencies, and the ordinate axis in the same represents intensities (transmission rates) of a signal, which pass through the band-pass filter. The graph of FIG. 16B shows a largest peak pattern around approximately 60 bpm (hereinafter, simplified as "peak pattern") and a plurality of sub-peaks. For example, the signal component at the frequency of 60 bpm can pass through the band-pass filter substantially without losing its intensity. Meanwhile, for example, intensities of signal components at the frequencies exceeding 110 bpm are attenuated by substantially 90% or more.

As shown in FIG. 16B, the band-pass filter allows the frequency components in the particular frequency band to pass therethrough, and removes the frequency components in the other bands. In this embodiment, a frequency band in which the intensities of the frequency components remain half or more is defined as a frequency band of each of the band-pass filters (pass bands). In other words, frequencies each having an attenuation amount of 50% respectively on a high frequency side and a low frequency side of the peak pattern are respectively an upper-limit frequency Gmax and a lower-limit frequency Gmin of each of the pass bands. Thus, a frequency G within the pass band is expressed by Gmin≤G≤Gmax, and a bandwidth ΔG of the pass band corresponds to a half width of the peak pattern (ΔG=Gmax−Gmin). Specifically, in the example shown in FIG. 16B, Gmax, Gmin, and ΔG are set respectively to 82 bpm, 28 bpm, and 54 bpm.

The frequency characteristics of the band-pass filters, such as the pass bands, are set as appropriate for removing the non-heart-rate component from the reference signal. Typically, the band-pass filters are set with reference to the heart-rate ranges shown in FIG. 15. In addition, the filter coefficients may be calculated such that the set pass bands exert their functions. In this embodiment, the pass bands are set to include the heart-rate ranges shown in FIG. 15. For example, the heart-rate ranges and the pass bands may match each other. The setting of the frequency characteristics of the band-pass filters is not limited thereto, and these frequency characteristics may be set as appropriate. Alternatively, a profile of the peak pattern may be set as appropriate in accordance with the pass bands.

In this way, the band-pass filters corresponding respectively to the heart-rate ranges can be selected from the plurality of filter coefficients stored in the first filter bank 62. Further, the pass bands of the band-pass filters, for example, are appropriately set in accordance with corresponding ones of the heart-rate ranges. With this, filtering can be properly performed in the respective heart-rate ranges, and hence the non-heart-rate component can be properly removed. Note that, the information items to be stored in the first filter bank 62, for example, are not limited, and the half width of the peak pattern, for example, may be stored in advance.

Figure 17:
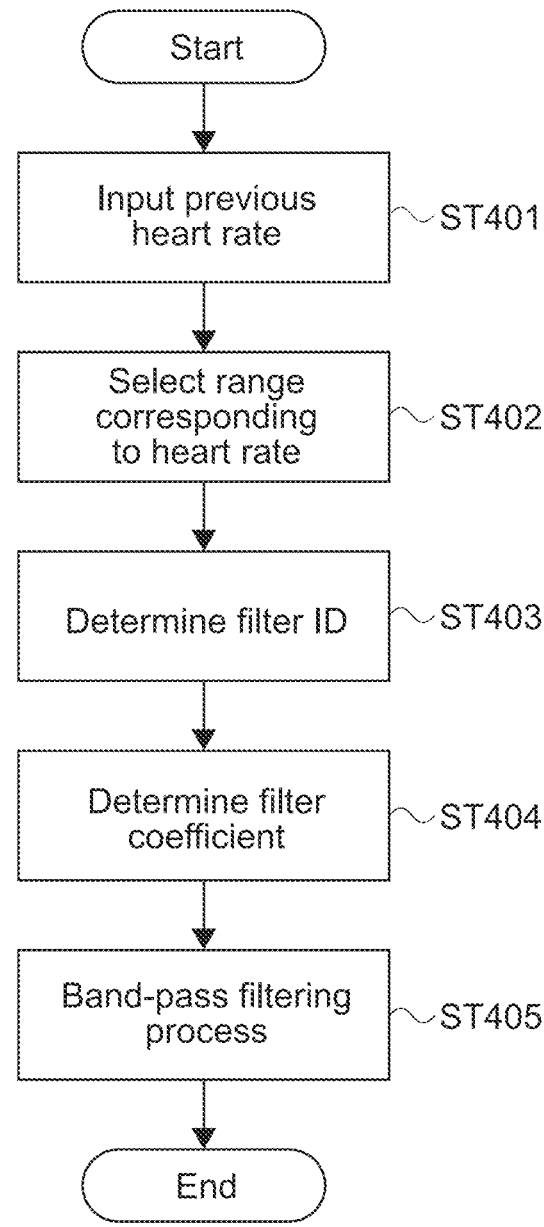
FIG. 17 A flowchart showing an example of a filtering procedure.

FIG. 17 is a flowchart showing an example of a filtering procedure. The immediately-preceding heart rate included in the heart-rate information item is input as the reference heart rate (Step 401). A range corresponding to the reference heart rate is selected from the first filter bank 62 (Step 402), and the filter ID is determined (Step 403).

The filter coefficient is determined from the filter ID (Step 404). The determined filter coefficient (hereinafter, described as "corresponding filter coefficient") is set as a filter coefficient of the filtering unit 61. In this way, the band-pass filter that allows the frequency band including the reference heart rate to pass therethrough is set in the filtering unit 61. In this embodiment, the pass band of the corresponding filter coefficient corresponds to a first frequency band.

In this embodiment, the adaptive-band-pass-filter processing unit 60 selects the corresponding filter coefficient corresponding to the reference heart rate. Then, the pass band of the corresponding filter coefficient is set as a frequency band of the filtering unit. In other words, the adaptive-band-pass-filter processing unit 60 sets the pass band on the basis of the heart-rate information item.

The filtering unit 61 executes the band-pass filtering process on the reference signal (Step 405). Of the frequency components contained in the second error signal, the frequency component within the pass band is allowed to pass. In other words, in accordance with the immediately-preceding heart rate (reference heart rate), the surrounding band components including the heart-rate component are allowed to pass, and the other bands are removed. Thus, the heart-rate component has been contained in the filtered second error signal (heart-rate component signal), and the non-heart-rate component has been removed therefrom.

Referring back to FIG. 3, on the basis of the pulse-wave signal (heart-rate component signal) output from the adaptive-band-pass-filter processing unit 60, a heart-rate fluctuation and a heart-rate trend are detected (Step 107). The heart-rate fluctuation is detected by the heart-rate-fluctuation detection unit 70 shown in FIG. 2. Further, the heart-rate trend is detected by a heart-rate-trend detection unit 80 shown in FIG. 2.

Figure 18:
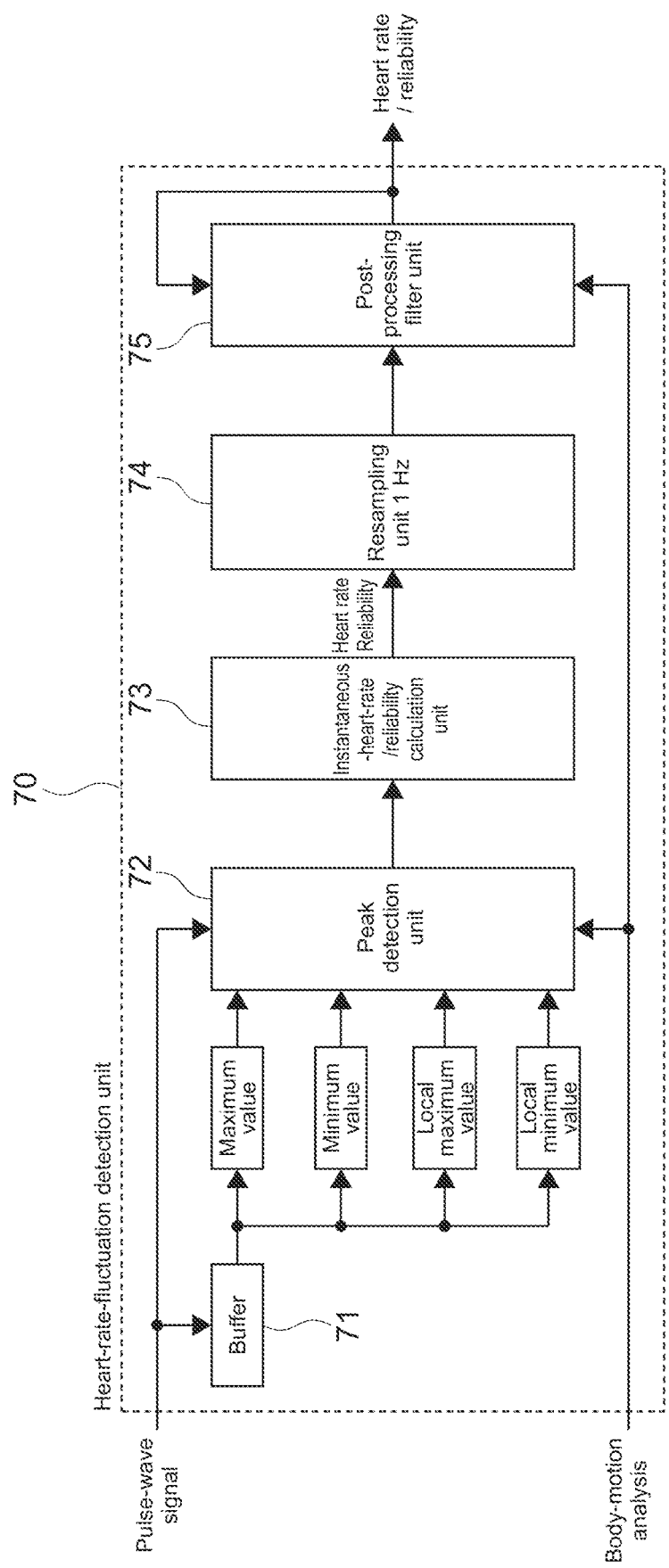
FIG. 18 A block diagram showing a configuration example of a heart-rate-fluctuation detection unit.

FIG. 18 is a block diagram showing a configuration example of the heart-rate-fluctuation detection unit 70. The heart-rate-fluctuation detection unit 70 includes a buffer 71, a peak detection unit 72, an instantaneous-heart-rate/reliability calculation unit 73, a resampling unit 74, and a post-processing filter unit 75.

In this embodiment, the peak detection unit 72 detects a peak position of the pulsation from the pulse-wave signal that has been reduced in body-motion noise. As shown in FIG. 18, a maximum value, a minimum value, a local maximum value, and a local minimum value of the pulse-wave signal are input to the peak detection unit 72 via the buffer 71. In the following, an example of peak-position detection by local-maximum-value detection is described.

Due to the body motion, the contact state of the first PPG sensor 12 may change to modulate an intensity of the pulse-wave signal. At this time, when peak detection is performed on the basis of a preset fixed threshold, the peak position of the pulsation may fail to be detected. Further, there is a risk that a false peak due to the body motion is falsely detected as the peak of the pulsation.

In this embodiment, in order that such errors in detection may not occur, as expressed by the following equation, a threshold "th" of a peak intensity is determined on the basis of a maximum value "vmax" and a minimum value "vmin" of a pulse-wave signal in a certain analysis window.

$$th = vmin + \alpha \cdot (vmax - vmin)$$

$$0 < \alpha < 1$$

With this, the threshold "th" of the peak intensity is adaptively controlled in accordance with the intensity of the pulse-wave signal. Thus, even when the intensity of the pulse-wave signal is modulated, the peak position can be detected.

Note that, even when such a threshold process is executed, residual body-motion noises at low-frequencies may cause the local maximum value with a small concavity (broad local-maximum value) to be falsely detected as the peak of the pulsation even when the peak intensity is high.

As a countermeasure, in this embodiment, any of or a plurality of the following processing examples are executed alone or in combination.

Calculating a concavity of a current local-maximum value, specifically, a level difference from an immediately-preceding local minimum value and an immediately-preceding local maximum value, and performing determination on the basis of the threshold.

In consideration of the modulation of the pulse-wave intensity due to the body motion, adaptively controlling the above-mentioned threshold in accordance with the first and/or the second body-motion analysis result.

Restricting a detection range of the local maximum value by setting the heart rate calculated by the heart-rate-trend detection unit 80 as a center of a search range. In this case, the heart-rate-fluctuation detection unit 70 and the heart-rate-trend detection unit 80 may be cascaded.

For example, by executing these processes, it is possible to suppress the false detection of the false peak due to the body-motion noises that cannot be completely removed by the noise removal in the first noise-reduction processing unit 30 and the second noise-reduction processing unit 40. As a result, accuracy of an instantaneous heart rate to be detected by the heart-rate-fluctuation detection unit 70 is increased.

The instantaneous-heart-rate/reliability calculation unit 73 detects the instantaneous heart rate and its reliability. The instantaneous heart rate, which means a momentary heart rate, is calculated, for example, as a value by multiplying an inverse of a time interval at the peak position (position of the local maximum value) by 60 (seconds). By calculating the instantaneous heart rate, the heart-rate fluctuation can be measured with high accuracy in real time during, for example, heart-rate training.

Note that, generally, the "heart rate" refers to the number of heartbeats at a time when a heart pumps out blood to an entirety of a body, and the "pulse rate" refers to the number of the pulsations (pulses) that occur in arteries. It is said that, as long as arrhythmia, pulse deficits, and the like do not occur, the "heart rate" and the "pulse rate" are substantially equal to each other. Herein, the results of the measurement by the heart-rate measurement device 200 are described, for example, as the heart-rate fluctuation, the heart-rate trend, and the instantaneous heart rate. Alternatively, the measurement results may be described, for example, as a pulse fluctuation, a pulse trend, and an instantaneous pulse rate. As a matter of course, the present technology is applicable, for example, also to a case where the "pulse rate" being the pulsations in the arteries at the measurement site is used as a parameter different from the "heart rate."

The reliability is calculated on the basis of, for example, the level difference between the local maximum value and the local minimum value. As the level difference between the local maximum value detected as the peak and the immediately-preceding (or immediately-subsequent) local minimum value, that is, a concavity of the local maximum value becomes larger, the reliability to be given becomes higher. The reliability may be calculated by other methods.

After resampling to 1 Hz by the resampling unit 74, the post-processing filter unit 75 executes a post-process thereon. For example, the post-processing filter unit 75 is constituted by an IIR filter and a feedback-factor calculation unit, and a feedback factor of this IIR filter is controlled as appropriate.

For example, the first noise-reduction processing unit 30, the second noise-reduction processing unit 40, and the peak detection unit 72 may fail to completely remove the noise. As a result, an outlier of a temporal change of the instantaneous heart rate may be generated. Generally, time correlation of the instantaneous heart rate is significantly high. Thus, when the temporal change of the instantaneous heart rate is larger than a preset threshold, adjustment of increasing the feedback factor of the IIR filter of the post-processing filter unit 75 (for example, to a value close to 1.0) is performed. With this, a previous instantaneous heart rate can be subjected as it is to an extrapolation process, whereby the false detection can be corrected (reduced). Further, on the basis of the analysis result from the body-motion analysis unit 20, during the exercise of the user, adjustment of a value of the feedback factor of the IIR filter to less than 1.0, specifically, to approximately 0.5, is performed. With this, the instantaneous heart rate can be stabilized.

Figure 19:
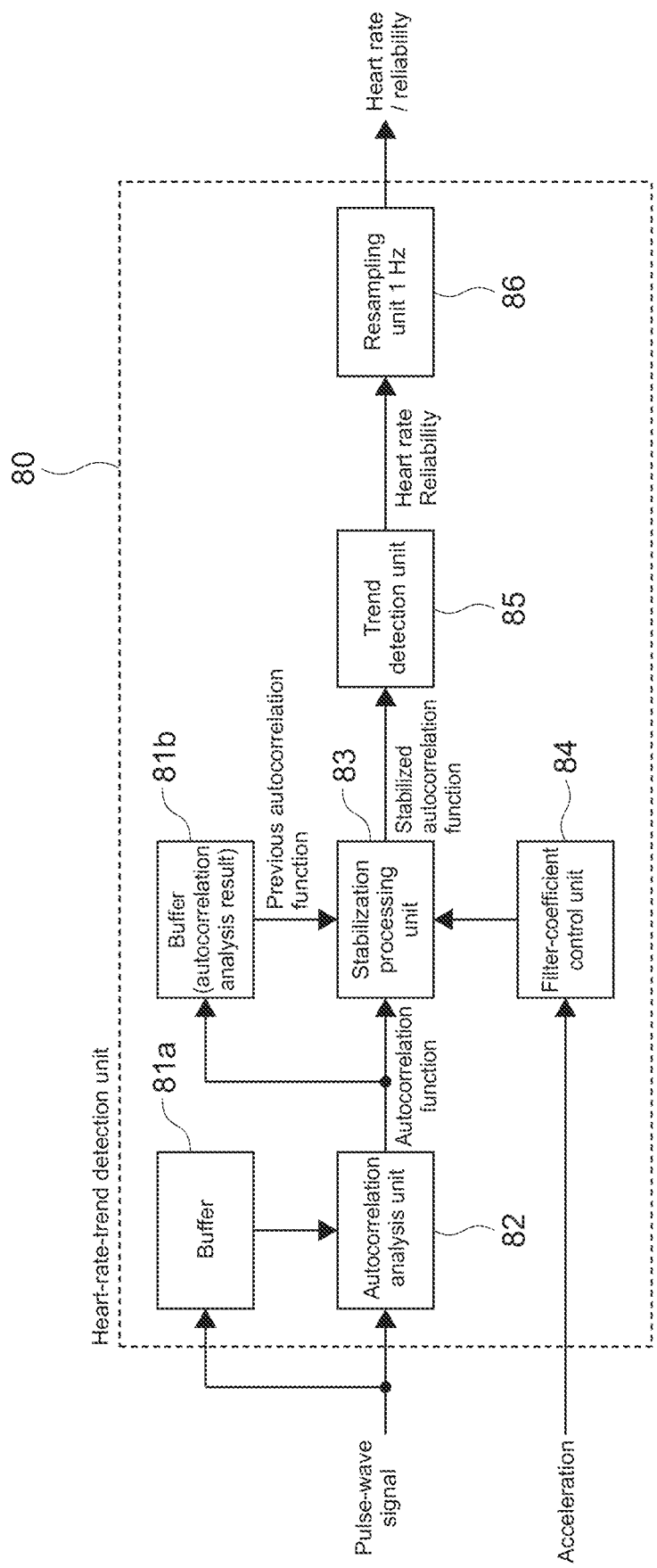
FIG. 19 A block diagram showing a configuration example of a heart-rate-trend detection unit.

FIG. 19 is a block diagram showing a configuration example of the heart-rate-trend detection unit 80. The heart-rate-trend detection unit 80 includes buffers 81*a* and 81*b*, an autocorrelation analysis unit 82, a stabilization processing unit 83, a filter-coefficient control unit 84, a trend detection unit 85, and a resampling unit 86.

The autocorrelation analysis unit 82 performs, at each sampling timing, autocorrelation analysis with respect to the pulse-wave signal that has been reduced in body-motion noise. Although there are various methods of calculating an autocorrelation function, a normalized autocorrelation function is used in the analysis to be performed in this embodiment.

The stabilization processing unit 83 performs weighting addition of a previous autocorrelation function stored in the buffer 81*b* with respect to an autocorrelation function at a current timing, thereby stabilizing the autocorrelation function. A weighting parameter is determined from the acceleration signal (body-motion signal) by the filter-coefficient control unit 84.

The trend detection unit 85 detects, from the stabilized autocorrelation function, lags τ during which an autocorrelation value consecutively increases. In this way, the trend detection unit 85 calculates periods of the pulse-wave signal as the heart-rate trend. On the basis of this heart-rate trend, the heart rate and its reliability are calculated. Note that, this heart rate is calculated on the basis of the heart-rate trend (periods of the pulse-wave signal), and hence is different from the instantaneous heart rate.

The reliability is calculated on the basis of, for example, normalized autocorrelation values at positions of the specified lags τ, that is, the autocorrelation values in the detected periods. As the autocorrelation value becomes larger, the reliability to be given becomes higher. The reliability may be calculated by other methods. After resampling to 1 Hz by the resampling unit 86, the heart rate and its reliability are output.

In this embodiment, the heart-rate-fluctuation detection unit 70 and the heart-rate-trend detection unit 80 correspond to a plurality of calculation units that calculate heart-rate-candidate information items and their reliabilities on the basis of the pulse-wave signal. Further, these detection units may be referred to also as heart-rate estimators. In addition, the instantaneous heart rate that is calculated by the peak detection, and the heart rate that is calculated by the autocorrelation analysis each correspond to the heart-rate-candidate information item.

The number of the calculation units that calculate the heart-rate-candidate information items on the basis of the pulse-wave signal, and algorithms for the calculation, and the like are not limited, and may be set as appropriate. Further, the heart rate is typically calculated as the heart-rate-candidate information item, but different information items may be calculated.

The integration processing unit 90 shown in FIG. 2 executes an integration process (Step 108). Specifically, on the basis of the instantaneous heart rate and the heart rate that are output as the heart-rate-candidate information items from each of the heart-rate-fluctuation detection unit 70 and the heart-rate-trend detection unit 80, and on the basis of their reliabilities, the integration processing unit 90 outputs the heart-rate information item. In other words, the integration processing unit 90 outputs a final heart-rate information item on the basis of output results from the plurality of heart-rate estimators and reliabilities of these results. In this embodiment, the integration processing unit 90 functions as an output unit.

As an example of methods of outputting the final heart-rate information item, there may be mentioned a heart-rate-candidate information item with a highest reliability. Specifically, the reliability of the instantaneous heart rate and the reliability of the heart rate based on the heart-rate trend are compared to each other, and then the heart rate with higher one of the reliabilities is output as the final heart-rate information item.

Alternatively, the final heart-rate information item (heart rate) may be calculated by multidimensional vectorization of the reliabilities calculated by the plurality of heart-rate estimators, and with use of, for example, a discriminator constituted by a neural network. When the neural network is established, a data item of an actual heart rate is obtained by measurement with, for example, an electrocardiograph. In this case, there are problems as long as a coefficient of the neural network is calculated by machine learning, with the multidimensional vectors calculated by the plurality of heart-rate estimators from the plurality of pulse-wave signals (pulse-wave signal and reference pulse-wave signal) and the acceleration signal (body-motion signal) that are measured simultaneously with each other being input data items.

Further, in this embodiment, the integration processing unit 90 determines whether or not to perform a fallback. For example, when both the reliability of the instantaneous heart rate and the reliability of the heart rate based on the heart-rate trend are lower than respective preset thresholds, the fallback is performed. As the fallback, for example, an immediately-preceding heart rate is pre-held, and output as the final heart-rate information item. With this, an output of the heart-rate information item with low reliability is prevented, and at the same time, the heart-rate measurement can be continued. Note that, an operation of the fallback is not particularly limited.

Further, on the basis of the reliabilities calculated by the first noise-reduction processing unit 30 and the second noise-reduction processing unit 40, whether or not the fallback operation needs to be performed may be determined. For example, when not only the reliabilities calculated by the first noise-reduction processing unit 30 and the second noise-reduction processing unit 40, but also the reliabilities calculated by the heart-rate-fluctuation detection unit 70 and the heart-rate-trend detection unit 80 are low, the fallback is performed. Alternatively, when the reliabilities calculated by the first noise-reduction processing unit 30 and the second noise-reduction processing unit 40 are low, the fallback is performed irrespective of values of the reliabilities calculated by the two heart-rate estimators. Still alternatively, when the reliabilities calculated by the first noise-reduction processing unit 30 and the second noise-reduction processing unit 40 are high, the fallback is not performed even when both the reliabilities calculated by the two heart-rate estimators are low, and the heart-rate-candidate information item with higher one of the reliabilities is output. Such processes also may be executed.

When a strength of fitting of the first PPG sensor 12 and the second PPG sensor 13 and the human skin is reduced by the body motion, external light beams and stray light beams may enter to cause the saturation of the pulse-wave signal. Further, the pulse-wave signal may be saturated also when the feedback light intensity changes due to a change in shape of the arm in conjunction with the body motion. In this embodiment, in order to avoid such risks, that is, to secure appropriate feedback-light intensities, the light intensities of light-emitting elements (light-emitting units) can be actively controlled (details of the light-intensity control are described below). In a case where the reliability of the pulse-wave signal is reduced or eliminated as a result of the light-intensity control, the fallback may be performed. Alternatively, whether or not the fallback operation needs to be performed may be determined on the basis of the reliabilities calculated by the body-motion analysis unit 20, or of a calculation value of the autocorrelation analysis by the heart-rate-trend detection unit 80.

The stabilization processing unit 100 stabilizes the heart rate to be output as the final heart-rate information item. For example, the stabilization processing unit 100 reduces the false detection of the instantaneous heart rate due to the body-motion noises that cannot be removed by the first noise-reduction processing unit 30, the second noise-reduction processing unit 40, and the peak detection. The configuration, for example, of the stabilization processing unit 100 is not particularly limited.

As shown in FIG. 2, the final heart-rate information item to be output from the stabilization processing unit 100 is fed back to the reference-signal generating unit 50 and the adaptive-band-pass-filter processing unit 60. However, a method, for example, of the feedback is not limited, and processes in accordance with types of the heart rate to be fed back may be executed as appropriate. For example, when the heart rate detected by the heart-rate-trend detection unit 80 is output as a final output, a consecutive heart rate that follows a previous trend is fed back. Thus, in this case, a value output from the stabilization processing unit 100 is fed back as it is to the first filter bank 62 and the second filter bank 54. Meanwhile, when the instantaneous heart rate detected by the heart-rate-fluctuation detection unit 70 is output, the instantaneous heart rate that abruptly changes is subjected, for example, to the smoothing process, and then fed back to the filter banks. In this way, filtering is performed stably in accordance with the feedback of the heart rate.

In this embodiment, the light-intensity control unit 110 shown in FIG. 2 controls the light intensity of the light beams in the first wavelength band, which are emitted from the first light-emitting unit of the first PPG sensor 12 (hereinafter, abridged as "light emission intensity"). The light-intensity control unit 110 corrects a light-intensity control value being a parameter for controlling the light emission intensity in accordance with a received-light intensity for the pulse-wave signal.

Figure 20:
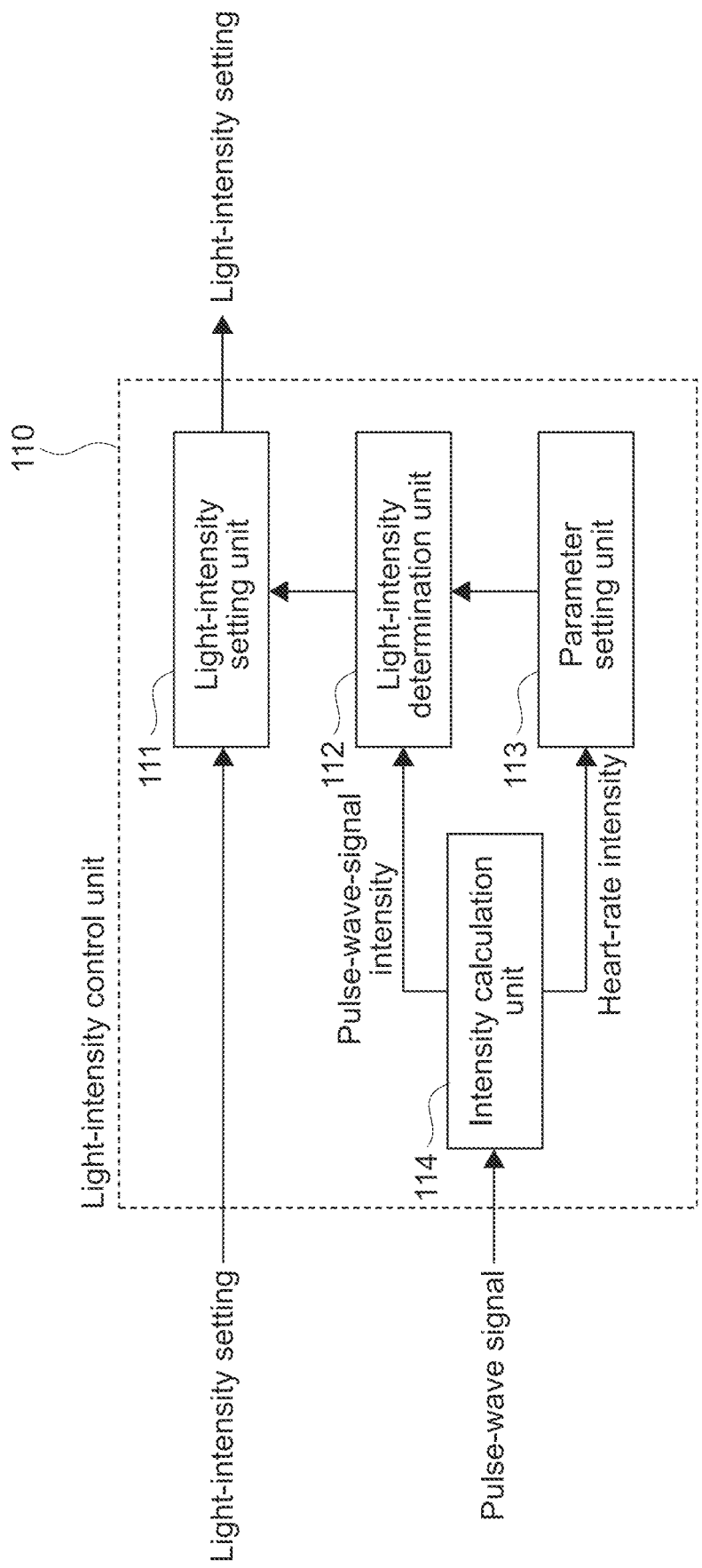
FIG. 20 A block diagram showing a configuration example of a light-intensity control unit.

FIG. 20 is a block diagram showing a configuration example of the light-intensity control unit. The light-intensity control unit 110 includes a light-intensity setting unit 111, a light-intensity determination unit 112, a parameter setting unit 113, and an intensity calculation unit 114. The light-intensity setting value for the first PPG sensor 12 is input to the light-intensity setting unit 111.

The pulse-wave signal (heart-rate component signal) output from the adaptive-band-pass-filter processing unit 60 is input to the intensity calculation unit 114. The pulse-wave signal contains an AC component that oscillates in periods equivalent to those of the heartbeat (hereinafter, abridged as "AC heart-rate component"), and other components. The intensity calculation unit 114 calculates a heart-rate intensity being an intensity of the AC heart-rate component, and a pulse-wave-signal intensity being the intensity of the pulse-wave signal itself.

The heart-rate intensity is an intensity of a signal based on the heartbeat, which is contained in the pulse-wave signal. The pulse-wave-signal intensity corresponds to an intensity of a baseline of the pulse-wave signal, which is a value in accordance, for example, with the feedback light intensity to be detected by the first light-receiving unit of the first PPG sensor 12. Generally, in the pulse-wave signal measured by the PPG, a value of the heart-rate intensity is smaller than that of the pulse-wave-signal intensity. Calculation methods, for example, for the heart-rate intensity and the pulse-wave-signal intensity are not limited. For example, an amplitude or an effective value of the AC heart-rate component is calculated as the heart-rate intensity. Further, as the pulse-wave-signal intensity, for example, an average value of the pulse-wave signal within a predetermined time period is calculated.

In this embodiment, in order to control the light emission intensity, a target value ("target") of the feedback light intensity, and a range in which reliable feedback-light intensities are obtained ("range") are determined. The "target" and the "range" each corresponding to the light-intensity control value are parameters to be used in the light-intensity determination unit 112.

The feedback light intensity herein refers to the intensity of the light beam detected by the first light-receiving unit of the first PPG sensor 12. The light beams to be detected by the first light-receiving unit may include not only the reflected light beams among the light beams in the first wavelength band, but also the external light beams and the stray light beams. Further, the first PPG sensor 12 outputs the pulse-wave signal with an intensity corresponding to the detected feedback-light intensity.

In this embodiment, the intensity of the pulse-wave signal output from the adaptive-band-pass-filter processing unit (pulse-wave-signal intensity) is used as an index that indicates the feedback light intensity. The index that indicates the feedback light intensity is not limited thereto. For example, the first PPG sensor 12 may directly measure the feedback light intensity. Alternatively, a pulse-wave signal, which is immediately after being output from the first PPG sensor 12 and has not been subjected, for example, to the filtering processes, may be used as the index that indicates the feedback light intensity.

Figure 21:
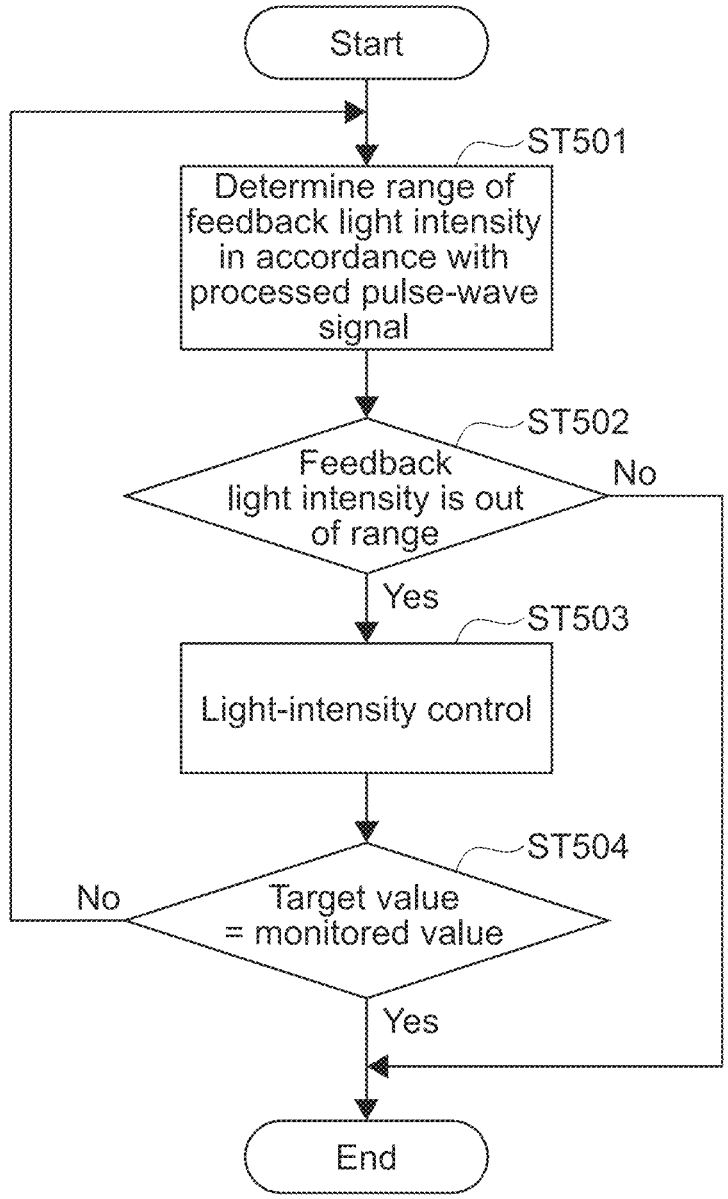
FIG. 21 A flowchart showing an example of light-intensity control.

FIG. 21 is a flowchart showing an example of the light-intensity control. First, the parameter setting unit 113 corrects a range of the feedback light intensity in accordance with the pulse-wave signal (Step 501). Specifically, the parameter setting unit 113 determines the light-intensity control values ("target" and "range") on the basis of the heart-rate intensity that the intensity calculation unit 114 has calculated from the pulse-wave signal. Details of a method of determining the light intensity are described below.

The light-intensity determination unit 112 determines whether or not the feedback light intensity is out of the range (Step 502). When the pulse-wave intensity signal calculated by the intensity calculation unit 114 falls within the feedback-light-intensity range ("range") determined in Step 501 (No in Step 502), the light-intensity control is ended. When the pulse-wave intensity signal does not fall within the "range" (Yes in Step 502), the light emission intensity is controlled.

The light-intensity setting unit 111 performs the light-intensity control (Step 503). In order that the feedback light intensity reaches the target value ("target") determined in Step 501, the light-intensity setting unit 111 performs proportional control (P control) on the light emission intensity of the first PPG sensor 12. For example, in accordance with a difference between the pulse-wave intensity and the "target," an increase or a decrease of the light emission intensity is calculated. On the basis of a current light-intensity setting value, and of the calculated increase or the calculated decrease, a new light-intensity setting value is calculated. Then, this new light-intensity setting value is output to the first PPG sensor 12.

The light-intensity determination unit 112 determines whether or not a monitored value of the feedback light intensity is equal to the target value ("target") (Step 504). This monitored value of the feedback light intensity is the pulse-wave-signal intensity calculated by the intensity calculation unit after the light-intensity control in Step 503. When the light-intensity determination unit 112 determines that the pulse-wave-signal intensity after the light-intensity control is not equal to the "target" (No in Step 504), the processes of Step 501 and subsequent Steps are re-executed to continue the light-intensity control. When the light-intensity determination unit 112 determines that the pulse-wave-signal intensity is equal to the "target" (Yes in Step 504), the light-intensity control is ended.

In this embodiment, on the basis of reference light-intensity control values (fixed parameters), the light-intensity control values (correction parameters) to be used in the light-intensity determination unit 112 is determined. A reference range in which reliable feedback-light intensities are obtained ("range0"), and a reference target value of the feedback light intensity ("target0") are set as the reference light-intensity control values. The "range0," which is a range defined by a reference lower-limit value "a" and a reference lower-limit value "b," is expressed as "range0={a, b}." The "target0" which is a reference lower-limit value "c," is expressed as "target0=c." "a," "b," and "c" are each the fixed parameter.

In this embodiment, the light-intensity control values are determined by gain-multiplying the fixed parameters "a," "b," and "c." The gains are calculated in accordance with the intensity of the AC heart-rate component (heart-rate intensity) $PPG_{ac}$, which is calculated by the intensity calculation unit 114, and a threshold $PPG_{th}$ of the heart-rate intensity.

Figure 22:
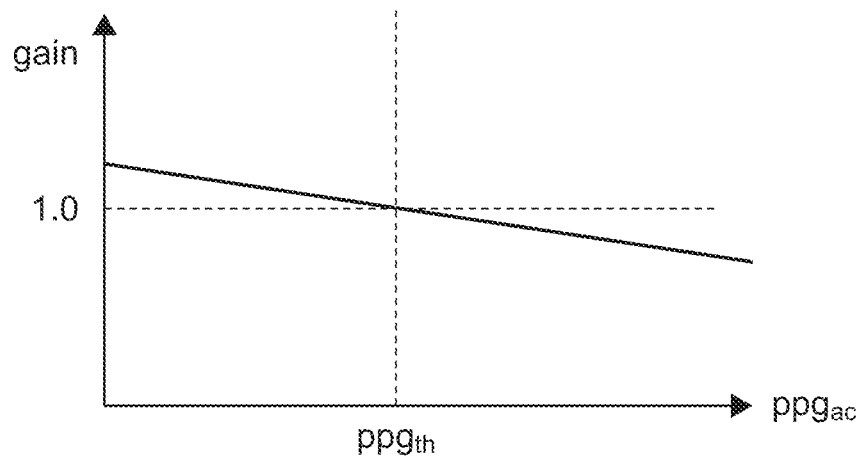
FIG. 22 A graph showing an example of gains to be used for correction of a range of a feedback light intensity.

FIG. 22 is a graph showing an example of the gains to be used for the correction of the range of the feedback light intensity. The abscissa axis and the ordinate axis of the graph respectively represent the heart-rate intensities and the gains. A relationship between the gains and the heart-rate intensities is expressed by "gain=f($PPG_{ac}$, $PPG_{th}$)." In the example shown in FIG. 22, the relationship between the gains and the heart-rate intensities is linear, and exhibits a negative slope. Further, when the heart-rate intensity $PPG_{ac}$ and the threshold $PPG_{th}$ are equal to each other, a value of the gain is one.

As shown in FIG. 22, when the heart-rate intensity $PPG_{ac}$ exceeds the threshold $PPG_{th}$, it is determined that a signal with a sufficiently high reliability has been detected, and a gain value less than one is selected. Thus, the light-intensity range (range in which reliable feedback-light intensities are obtained) and the target light-intensity value (target value of the feedback light intensity) are reduced by being gain-multiplied.

When the heart-rate intensity $PPG_{ac}$ is less than the threshold $PPG_{th}$, it is determined that a signal with a low reliability has been detected, and a gain value more than one is selected. Thus, the light-intensity range and the target light-intensity value are increased by being gain-multiplied.

In this way, in accordance with the heart-rate intensities, the reference fixed parameters are corrected as appropriate. Specifically, by gain-multiplying the fixed parameters "a," "b," and "c," correction parameters a' b' and c' are respectively determined. More specifically, a lower-limit value "a'=gain×a," an upper-limit value "b'=gain×b," and a target value "c'=gain×c" are calculated. Final values of the correction parameters are determined by a clipping process described below.

In this embodiment, the correction parameters are calculated in consideration, for example, of a dynamic range of the first light-receiving unit of the first PPG sensor 12. For example, light beams exceeding an upper limit of the dynamic range cause deterioration of the light receiving unit. Meanwhile, when the light intensity is excessively low, it is difficult to detect a pulse-wave component. Thus, a maximum allowable value and a minimum allowable value of each of the correction parameters are set in advance, and the clipping process is executed such that the correction parameters fall within ranges therebetween. The maximum value and the minimum value of each of the correction parameters are set as appropriate in accordance, for example, with characteristics of the first light-receiving unit.

For example, the fixed parameter "a" is stored in advance together with a maximum value $a_{max}$ and a minimum value $a_{min}$. The clipping process is executed to set an upper limit of a' to $a_{max}$ when the fixed parameter "a" exceeds the maximum value $a_{max}$ by being gain-multiplied, and to set a lower limit of a' to $a_{min}$ when the fixed parameter "a" falls below the minimum value $a_{min}$ by being gain-multiplied. The fixed parameters "b" and "c" are also stored in advance together with their maximum values and minimum values, and similarly subjected to the clipping processes. The clipping processes to be executed on the parameters are expressed as follows.

$$a'=\text{clip}(\text{gain}\times a, a_{min}, a_{max})$$

$$b'=\text{clip}(\text{gain}\times b, b_{min}, b_{max})$$

$$c'=\text{clip}(\text{gain}\times c, c_{min}, c_{max})$$

The correction parameters that have been subjected to the clipping processes are set as final light-intensity control values. Specifically, "range={a', b'}" is set as the range in which reliable feedback-light intensities are obtained, and "target=c'" is set as the target value of the feedback light intensity. In Step 502 and Step 504, the pulse-wave-signal intensity is determined on the basis of the "range" and the "target" that have set by the light-intensity determination unit 112.

The light-intensity setting value calculated in Step 503 is output also to the body-motion analysis unit 20 shown in FIG. 2. With this, the body-motion analysis unit 20 is allowed to calculate the reliabilities of, for example, the pulse-wave signal on the basis of a latest light-intensity setting value. Note that, when the light-intensity control and the like are not performed, a light-intensity setting value output, for example, from the first PPG sensor 12 is output as it is to the body-motion analysis unit 20.

In this embodiment, the gain values are set on the basis of a linear function. Instead, the gain values may be set, for example, by using a line chart or curve functions such as a Sigmoid function. Further, in this embodiment, the gain values given to the fixed parameters "a," "b," and "c" are equal to each other. Instead, individual gain values may be given respectively to the fixed parameters by respectively setting different gain-value control graphs.

In this way, in this embodiment, by utilizing the intensity of the weak AC heart-rate component contained in the pulse-wave signal, the range of the feedback light intensity that the pulse-wave sensor detects is corrected, and the light emission intensity is controlled. For example, adjustment of the value of the feedback light intensity to a constant value by methods including using the fixed parameters, such as the P control that is generally performed in the field of a control engineering, is performed, but it is difficult to properly maintain other parameters thereby. Meanwhile, by performing the control of correcting the fixed parameters, the range of the feedback light intensity can be adjusted. With this, the light intensity and the like can be controlled such that the parameters other than the feedback light intensity (such as heart-rate intensity) reach appropriate values.

As described hereinabove, in the heart-rate measurement device 200 according to this embodiment, the adaptive-band-pass-filter processing unit 60 filters the pulse-wave signal on the basis of previous heart-rate information items. Then, highly accurate heart-rate information items are output on the basis of the filtered pulse-wave signal. In this way, highly accurate heart-rate measurement can be performed.

Various body motions occur during activities of the user. When the body motions occur in a daily environment, it is conceived that body-motion noises over a wide range from a low-frequency band to a high-frequency band occur. Further, the user does the variety of activities in his/her daily environment, and hence body-motion noises occur in various patterns and with various intensities, specifically, a periodic body-motion noise and a non-periodic body-motion noise occur.

When heart-rate measurement is performed in the daily environment, the body-motion noises of various types are contained in the output from, for example, the pulse-wave sensor. When such body-motion noises cannot be completely removed, an S/N ratio of the heart-rate component decreases, which may be factors that cause errors in detecting the heartbeat.

In the heart-rate measurement device 200 according to this embodiment, the adaptive-band-pass-filter processing unit 60 functions as the band-pass filter. At this time, the pass band of the band-pass filter is set on the basis of the heart rate that is immediately-previously output from the heart-rate measurement device 200 (stabilization processing unit 100).

In this way, by setting the pass band by feeding back a value of the immediately-previously-detected heart rate, the band-pass filter that adaptively operates in accordance, for example, with the heart-rate fluctuation is provided. With this, a frequency band relating to a heart rate to be measured can be extracted. Thus, even when the periodic or the non-periodic body-motion noise is mixed, a signal in which the S/N ratio of the heart-rate component is kept high can be output. With this, highly accurate heart-rate measurement can be performed in accordance with various scenes in daily life.

Further, in this embodiment, the reference signal filtered by the adaptive-band-elimination-filter processing unit 52 being the second filter unit is generated. For example, it is assumed that the reference pulse-wave signal from the second PPG sensor 13 is used as the reference signal. The reference pulse-wave signal contains not only a lot of information items of the body-motion noise that is caused by the movements of the fingers and the wrist, but also the heart-rate component. Thus, it is conceived that, when the body-motion noise in the pulse-wave signal, which is caused by the movements of the fingers and the wrist, is reduced, the heart-rate component is also weakened at the same time, resulting in a decrease of the S/N ratio of the heart-rate component.

In the reference-signal generating unit 50, the adaptive-band-elimination-filter processing unit 52 functions as the band-elimination filter. The stop band of the band-elimination filter is set on the basis of the fed-back heart rate. With this, the heart-rate component contained in the reference signal can be removed with high accuracy, and hence the body-motion noise in the pulse-wave signal can be sufficiently reduced without weakening the heart-rate component. Further, at the time of using the body-motion signal (acceleration) the reference signal, even when a frequency band of the body-motion and a frequency band of the pulses match each other, the body-motion noise can be removed without reducing the S/N ratio of the heart-rate component.

In the peak detection by the heart-rate-fluctuation detection unit 70, the peak position of the pulsation can be detected. Thus, the heart-rate fluctuation can be detected with high accuracy. Meanwhile, in the autocorrelation analysis by the heart-rate-trend detection unit 80, periodicity of the pulse wave is utilized. Thus, it is difficult to detect the heart-rate fluctuation with high accuracy. However, in the autocorrelation analysis, the risk that the peak due to the residual noise is falsely detected as the peak position of the pulsation can be sufficiently suppressed. With this, significantly-high noise resistance is obtained. By preparing the plurality of heart-rate estimators having characteristics different from each other in this way, and on the basis of the reliabilities to be obtained therefrom, the final heart-rate information item is calculated. As a result, heart-rate detection in which disadvantages of the units are compensated each other can be performed, and hence heart-rate measurement with accuracy significantly higher than that in a case of using a single heart-rate estimator is performed.

Further, although the PPG heart-rate sensor is capable of measuring the pulse-wave signal with relatively high accuracy in the resting state, once the measurement site moves, the body-motion noises are generated in the monitoring signal. As examples of a factor of the body-motion noises in the wristband-type heart-rate sensor, entry of unnecessary reflection from a surface of the skin, and the entry of the external light beams that have propagated under the skin may be mentioned, which are caused by the change of the contact state of the PPG sensor and the measurement site. Further, even when the contact state of the PPG sensor and the measurement site is satisfactory, the false signals may be generated by the blood-flow changes due to the movement of the measurement site, and a fluctuation of a light absorption rate may be caused by the deformation of the tissues under the skin due to the movements of the fingers and the wrist (movements of bones). Such risks may be mentioned as other examples of the factor. When, for example, a combined factor of these main factors causes mixing of a false peak signal into the pulse-wave signal, it is difficult to distinguish which peak corresponds to the peak position of the pulsation. As a result, at a time of calculating the instantaneous heart rate from a time difference between peak positions, there arises a risk that an erroneous pulse rate is detected.

As an example of advantageous techniques for reducing the body-motion noises as described above, the above-described adaptive filtering may be mentioned. Now, the adaptive filtering is described again. The adaptive filtering is a technique for automatically calculating a filter coefficient (W) that minimizes power of an error signal (e) at a time when a monitoring signal (d) and an input signal (X) are given is minimized. When the monitoring signal is the pulse-wave signal, a noise mixed with the monitoring signal can be separated by referring to the input signal, specifically, to a signal having high correlation with the noise.

In the heart-rate measurement device 200 according to this embodiment, the first noise-reduction processing unit 30 reduces the arm movement noise, and the second noise-reduction processing unit 40 reduces the finger-and-wrist movement noise. Thus, both the noise due to the cyclic movement of the arm, which are typified by those during walking and running, and the noise due to the non-cyclic movements such as those of the fingers and the wrist can be sufficiently reduced.

Further, when the filtering by the adaptive-band-pass-filter processing unit 60 can be performed in combination, a noise due to a non-cyclic movement of the arm at times other than the walking and the running also can be reduced. With this, even during movements in the daily living environment, such as those in resting states (inactivity such as sleeping), level-resting states (dining, washing, deskwork, and operating a smartphone), and during activities (running and walking), the noise reduction processes in which the false detection is prevented can be executed. As a result, the heart-rate fluctuation in the daily life can be constantly measured with high accuracy.

By performing the feedback on the basis of previous heart-rate determination results (heart-rate information items) supported by the highly accurate heart-rate measurement as described above, accuracy of the filtering can be increased. With this, a heart rate with sufficiently high accuracy can be output on the basis of the filtering with the increased accuracy. In this embodiment, by providing, for example, the first filter unit and the second filter unit in addition to the first noise-reduction processing unit and the second noise-reduction processing unit, a positive cycle in which highly accurate heart-rate measurement is performed in any situation is made.

In this embodiment, the light-intensity control unit 110 controls the light emission intensity of the first PPG sensor 12 on the basis of the heart-rate intensity. Specifically, when a sufficiently high heart-rate intensity has been detected, the light emission intensity is reduced such that the heart-rate intensity is moderated. In contrast, when the heart-rate intensity is low, the light emission intensity is increased to perform adjustment to an appropriate heart-rate intensity. With this, the appropriate heart-rate intensity can be maintained while suppressing, for example, unnecessary light-emission. Thus, both robustness in detection of the heart-rate fluctuation and low power consumption can be achieved.

Frequency analysis techniques also have been known as techniques for stably calculating the pulse rate. Specifically, by performing frequency analysis with respect to the pulse-wave signal after the noise reduction processes, a frequency at which a maximum spectrum intensity is obtained is determined as the pulse rate. However, the frequency analysis techniques have a problem in principle with accuracy in estimating the heart-rate fluctuation in a low-heart-rate band. In the heart-rate measurement device 200 according to this embodiment, even the heart-rate fluctuation in the low-heart-rate band can be calculated with high accuracy.

In this embodiment, the heart-rate measurement device 200 is described as one embodiment of the vital sign processing device according to the present technology. The embodiment of the vital sign processing device according to the present technology is not limited thereto, and encompasses arbitrary devices including the pulsimeter. For example, arbitrary electronic apparatuses, specifically, wearable devices of various types such as a headband type, a neckband type, and a belt type, arbitrary PDAs (Personal Digital Assistants) such as a smartphone and a tablet terminal, medical devices, game devices, and home electric appliances may be configured as the vital sign processing device according to the present technology.

Further, a wearable device, a mobile device, and the like that have only the functions of the controller 15 shown in FIG. 1B may be configured as an information processing device according to the present technology. In this case, for example, an I/F (interface) to be connected to the pulse-wave sensor functions as an acquisition unit that acquires the pulse-wave signal.

Second Embodiment

A heart-rate measurement device according to a second embodiment of the present technology is described. Hereinbelow, description of the same configurations and the same functions as those in the heart-rate measurement device 200 according to the above-described embodiment is omitted or simplified.

In the first embodiment, the pulse-wave signal (second error signal) from which the body-motion noises have been separated by the first noise-reduction processing unit 30 and the second noise-reduction processing unit 40 is filtered by the adaptive-band-pass-filter processing unit 60 provided in a subsequent stage. In contrast, in this embodiment, the adaptive-band-pass-filter processing unit is provided in a stage preceding the noise-reduction processing units.

Figure 23:
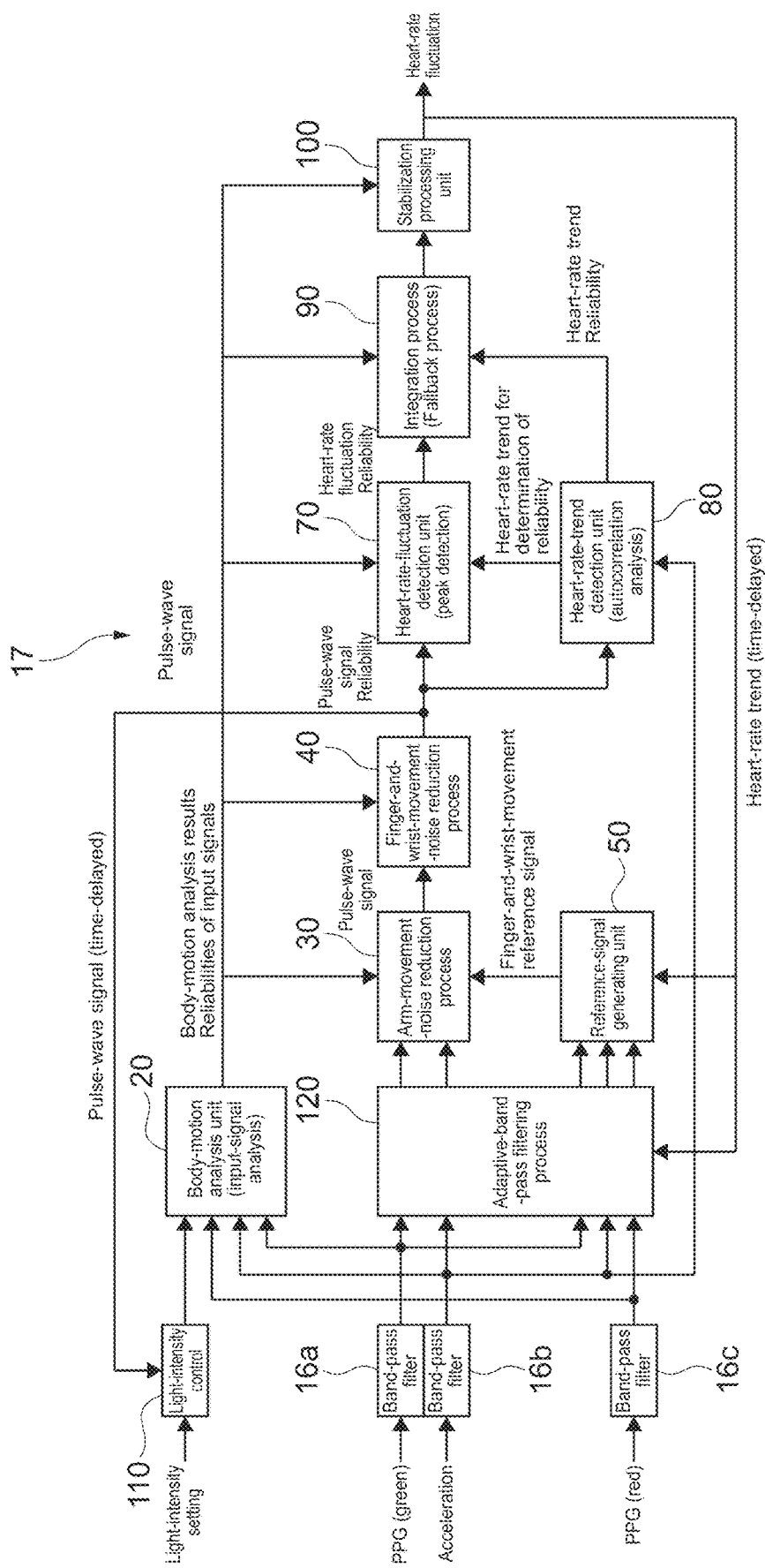
FIG. 23 A block diagram showing a functional configuration example of a controller according to a second embodiment.

FIG. 23 is a block diagram showing a functional configuration example of a controller according to the second embodiment. In a controller 17 shown in FIG. 23, an adaptive-band-pass-filter processing unit 120 is provided in a stage preceding the first noise-reduction processing unit 30 (arm-movement-noise-reduction processing unit 30) and the reference-signal generating unit 50.

The pulse-wave signal (PPG (green)) output from the first PPG sensor 12, the reference pulse-wave signal (PPG (red)) output from the second PPG sensor 13, and the body-motion signal (acceleration) output from the acceleration sensor 14 are input to the adaptive-band-pass-filter processing unit 120. Further, the heart-rate information item (reference heart rate) output from the stabilization processing unit 100 is input to the adaptive-band-pass-filter processing unit 120.

Figure 24:
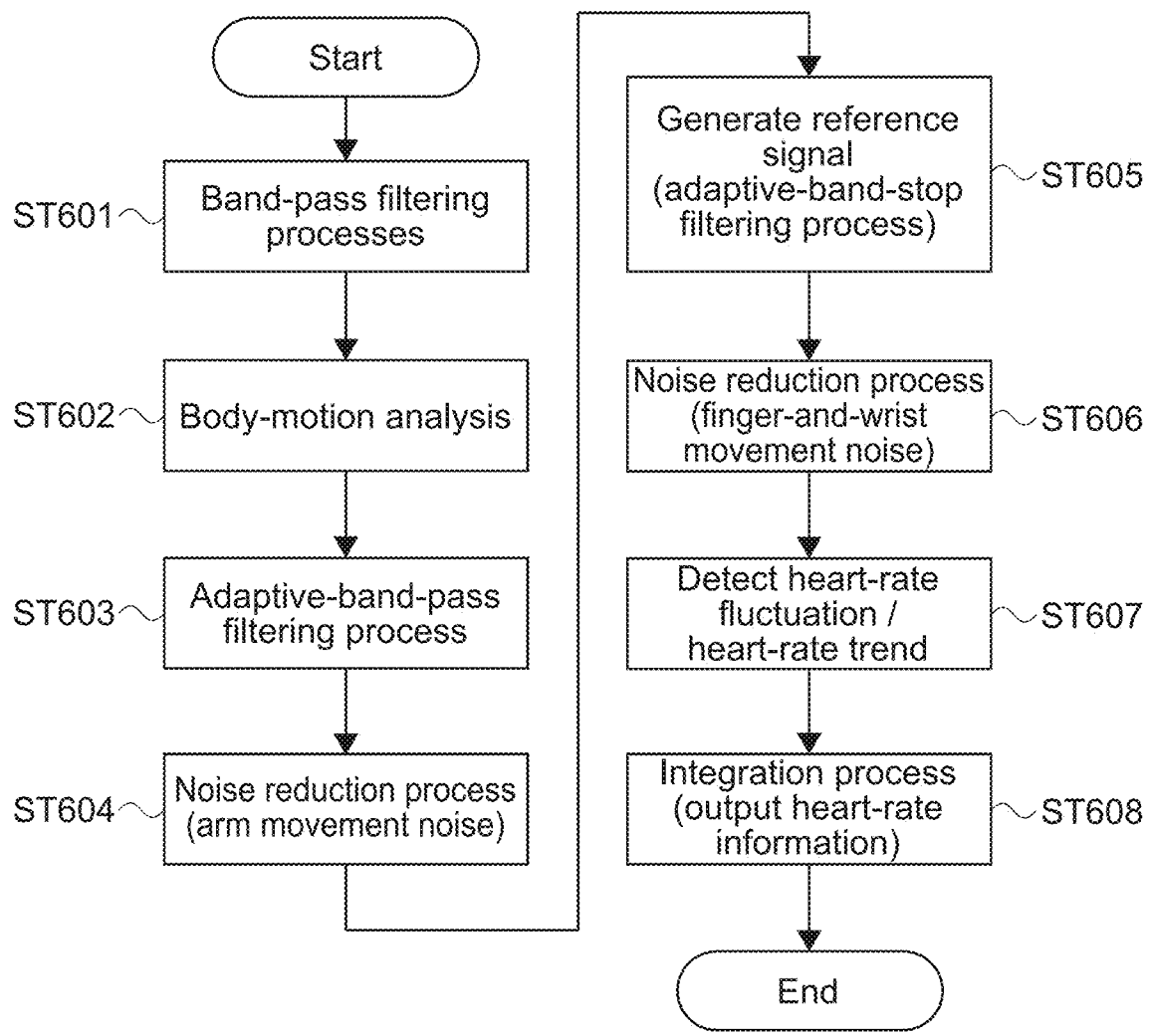
FIG. 24 A flowchart showing another example of outputting the heart-rate information item.

FIG. 24 is a flowchart showing another example of outputting the heart-rate information item. First, the band-pass filters 16a to 16c execute the band-pass filtering processes (Step 601). The body-motion analysis unit 20 analyzes the body-motion intensity at the measurement site (Step 602).

The adaptive-band-pass-filter processing unit 120 shown in FIG. 23 performs filtering on the basis of an immediately-preceding heart rate (Step 603). The adaptive-band-pass-filter processing unit 120 executes the processes of filtering, through the respective band-pass filters, the pulse-wave signal to be input, the reference pulse-wave signal to be input, and the body-motion signal to be input. The band-pass filters allow the surrounding band including the reference heart rate (first frequency band) to pass therethrough, and remove the other frequency bands.

In this embodiment, a plurality of band-pass filters (filtering units) are provided correspondingly to the signals to be input, and these signals are respectively filtered thereby. Specifically, the non-heart-rate components are removed from the pulse-wave signal, the body-motion signal, and the reference pulse-wave signal output from the band-pass filters 16a to 16c. With this, with respect to all the signals for generating the heart-rate information items and the like, frequency regions of the non-heart-rate component are removed, and only the surrounding band including the heart-rate component can be maintained. Thus, highly accurate processes focused on a limited frequency band can be executed.

The signals that have passed through the band-pass filters are transmitted to the blocks in the subsequent stage. For example, the filtered reference signal and the filtered body-motion signal are output to the first noise-reduction processing unit 30. Further, for example, all the filtered pulse-wave signal, the filtered body-motion signal, and the filtered reference pulse-wave signal are output to the reference-signal generating unit 50.

The first noise-reduction processing unit 30 shown in FIG. 23 executes the arm-movement-noise reduction process (Step 604). The first noise-reduction processing unit 30 reduces the arm movement noise in the pulse-wave signal from which the non-heart-rate component has been removed, and then outputs the first error signal (pulse-wave signal).

The reference-signal generating unit 50 generates the reference signal (Step 605). The reference-signal generating unit 50 performs, for example, the main-component analysis of the pulse-wave signal, the body-motion signal, and the reference pulse-wave signal from each of which the non-heart-rate component has been removed. On the basis of this analysis, the reference signal that has high correlation with the finger-and-wrist movement noise is generated.

The adaptive-band-elimination-filter processing unit (second filter unit) filters the reference signal with reference, for example, to the second filter bank. With this, the heart-rate component is removed from the reference signal. As a result, the reference signal that has high correlation with the finger-and-wrist movement noise and low correlation with the heart-rate component being a main signal is generated. The filtered reference signal is output to the adaptive filter of the second noise-reduction processing unit.

The second noise-reduction processing unit 40 executes the finger-and-wrist-movement-noise reduction process (Step 606). In the second noise-reduction processing unit 40, the reference signal filtered by the second filter unit is input to the adaptive filter. The output value of the adaptive filter is subtracted from the first error signal, and then the second error signal (pulse-wave signal) is output. The second error signal is a signal in which both the body-motion noises, specifically, the arm movement noise and the finger-and-wrist movement noise have been reduced and from which the non-heart-rate component has been removed.

On the basis of the second error signal, the heart-rate fluctuation and the heart-rate trend are detected (Step 607). The heart-rate-fluctuation detection unit 70 and the heart-rate-trend detection unit 80 detect the instantaneous heart rate and the heart rate based on the heart-rate trend. The integration processing unit 90 executes the integration process (Step 608), and then the stabilization processing unit 100 outputs the final heart rate. The final heart rate is fed back as appropriate to the adaptive-band-pass-filter processing unit 120 and the reference-signal generating unit 50.

In this way, before the body-motion noises are reduced, the adaptive-band-pass-filter processing unit 120 according to this embodiment removes the non-heart-rate component from each of the signals. With this, the processes can be executed intensively on the band including the heart-rate component. Thus, for example, the processes in the subsequent stages are allowed to progress with higher accuracy than that at a time when a wide frequency band is processed. Specifically, the number of calculations to be performed can be reduced, and hence processing time periods, for example, can be shortened.

Further, the reference signal is generated via the adaptive-band-pass-filter processing unit and the adaptive-band-elimination-filter processing unit (first filter unit and second filter unit). With this, the correlation between the heart-rate component being the main signal to be extracted and the reference signal is minimized. Thus, substantially without reducing the heart-rate component, the noises due to the body motions can be separated. As a result, accuracy of the calculations for separating the body-motion noises is increased, and hence a signal containing an emphasized heart-rate component can be generated. In this way, highly accurate heart-rate measurement can be performed.

Other Embodiments

The present technology is not limited to the embodiments described hereinabove, and various other embodiments may be carried out.

In the first embodiment and the second embodiment, the reference signal generated by the signal analysis unit of the reference-signal generating unit is filtered by the adaptive-band-elimination-filter processing unit (second filter unit). Note that, for example, the order of removing the heart-rate component from the reference signal is not limited as long as the heart-rate component is removed at an arbitrary timing before the reference signal is used for the separation of the body-motion noises.

Specifically, the second filter unit may be provided in a stage preceding the signal analysis unit. In other words, after the second filter unit filters the pulse-wave signal, the reference pulse-wave signal, and the body-motion signal, the signal analysis unit may generate the reference signal on the basis of these filtered signals. With this, for example, by performing the main-component analysis intensively on the non-heart-rate component including the body-motion noise component at a high rate, comparisons, analyses, and the like of the signals can be performed with high accuracy. Thus, the reference signal that has high correlation with the body-motion noises and low correlation with the heart-rate component can be generated. With this, the noise reduction processes can be executed with high accuracy. Herein, the filtering of the reference signal encompasses the generation of the reference signal from the filtered pulse-wave signal, the filtered reference pulse-wave signal, and the filtered body-motion signal.

Hereinabove, the first PPG sensor 12 is provided to generate the pulse-wave signal, and the second PPG sensor 13 is provided to generate the reference pulse-wave signal for generating the reference signal. Instead, either one of the pulse-wave-candidate signals to be output from the first PPG sensor 12 and the second PPG sensor 13 may be selected as appropriate, and output as the pulse-wave signal from which the heart rate is calculated.

For example, when feedback light intensities of the two pulse-wave-candidate signals to be output from the first PPG sensor 12 and the second PPG sensor 13 are equalized to each other, one with a more intense pulse-wave component is selected as the main signal, and the subsequent noise-reduction processes are executed on this pulse-wave-candidate signal. In other words, a first pulse-wave sensor that generates the pulse-wave signal to be subjected to the noise reduction processes may be predetermined from a plurality of pulse-wave sensors, or the first pulse-wave sensor may be selected as appropriate from the plurality of pulse-wave sensors. By selecting the first pulse-wave sensor each time, a signal with a most intense pulse-wave component can be selected. With this, highly accurate heart-rate measurement can be performed.

At least two of the features described hereinabove according to the present technology may be combined with each other. In other words, various features described in the embodiments may be arbitrarily combined with each other regardless of the embodiment. Further, the various advantages described hereinabove are merely examples, and hence are not limited thereto. Thus, other advantages may be additionally obtained.

Note that, the present technology may also employ the following configurations.

(1) A vital sign processing device, including:
 a pulse-wave sensor unit that outputs a pulse-wave signal;
 an output unit that outputs a heart-rate information item on the basis of the output pulse-wave signal; and
 a first filter unit
  that sets a first frequency band on the basis of the output heart-rate information item, and
  that allows the set first frequency band of the pulse-wave signal to pass through the first filter unit.

(2) The vital sign processing device according to Item (1), in which
 the first filter unit sets the first frequency band on the basis of a heart rate included in the heart-rate information item.

(3) The vital sign processing device according to Item (2), in which
the first filter unit
includes a first filter bank including a plurality of band-pass filters, and
selects, on the basis of the heart rate and from the first filter bank, a filter that allows the first frequency band to pass through the filter.
(4) The vital sign processing device according to any one of Items (1) to (3), further including
a plurality of calculation units, each of which calculates a heart-rate-candidate information item and a reliability of the heart-rate-candidate information item on the basis of the output pulse-wave signal, in which
the output unit outputs the heart-rate information item on the basis of the heart-rate-candidate information item and the reliability of the heart-rate-candidate information item, the heart-rate-candidate information item and the reliability being calculated by each of the plurality of calculation units.
(5) The vital sign processing device according to Item (4), in which
each of the plurality of calculation units calculates the heart-rate-candidate information item and the reliability of the heart-rate-candidate information item on the basis of the pulse-wave signal filtered by the first filter unit.
(6) The vital sign processing device according to Item (4) or (5), further including:
a body-motion sensor that outputs a body-motion signal; and
a noise-reduction processing unit that separates, on the basis of the body-motion signal, a body-motion noise from the pulse-wave signal output from the pulse-wave sensor unit, in which
each of the plurality of calculation units calculates the heart-rate-candidate information item and the reliability of the heart-rate-candidate information item on the basis of the pulse-wave signal from which the body-motion noise has been separated.
(7) The vital sign processing device according to Item (6), in which
the first filter unit filters the pulse-wave signal from which the body-motion noise has been separated by the noise-reduction processing unit.
(8) The vital sign processing device according to Item (6) or (7), in which
the pulse-wave sensor unit
includes a plurality of pulse-wave sensors, and
outputs, as the pulse-wave signal, any one of a plurality of pulse-wave-candidate signals that are generated by the plurality of pulse-wave sensors.
(9) The vital sign processing device according to Item (8), further including
a generating unit that generates, on the basis of the plurality of pulse-wave-candidate signals that are generated by the plurality of pulse-wave sensors, a reference signal for separating the body-motion noise, in which
the noise-reduction processing unit
includes an adaptive filter to which the reference signal is input as an input signal, and
outputs an error signal obtained by subtraction of an output value of the adaptive filter from the pulse-wave signal.
(10) The vital sign processing device according to Item (9), further including
a second filter unit
that sets a second frequency band on the basis of the heart-rate information item output by the output unit, and
that removes the set second frequency band of the reference signal.
(11) The vital sign processing device according to Item (10), in which
the second filter unit sets the second frequency band on the basis of a heart rate included in the heart-rate information item.
(12) The vital sign processing device according to Item (11), in which
the second filter unit
includes a second filter bank including a plurality of band-elimination filters, and
selects, on the basis of the heart rate and from the second filter bank, a filter that removes the second frequency band.
(13) The vital sign processing device according to any one of Items (10) to (12), in which
the second filter unit filters at least one of the plurality of pulse-wave-candidate signals or the body-motion signal, and
the generating unit generates the reference signal on the basis of an output from the second filter unit.
(14) The vital sign processing device according to any one of Items (10) to (13), in which
the generating unit generates the reference signal on the basis of the plurality of pulse-wave-candidate signals filtered by the first filter unit, and
the noise-reduction processing unit outputs an error signal obtained by subtraction of the output value of the adaptive filter from the pulse-wave signal filtered by the first filter unit.
(15) The vital sign processing device according to Item (14), in which
the second filter unit
filters the reference signal generated by the generating unit, and
then outputs the filtered reference signal to the adaptive filter.
(16) The vital sign processing device according to any one of Items (8) to (15), in which
the plurality of pulse-wave sensors include a pulse-wave-signal pulse-wave sensor that generates the pulse-wave signal by emitting light beams in a predetermined wavelength band and then detecting a reflected light beam among the light beams in the predetermined wavelength band, and
the vital sign processing device further includes
a light-intensity control unit that controls, on the basis of the pulse-wave signal filtered by the first filter unit, light intensities of the light beams in the predetermined wavelength band, the light beams being emitted from the pulse-wave-signal pulse-wave sensor.
(17) The vital sign processing device according to Item (16), in which
the light-intensity control unit controls the light intensities of the pulse-wave-signal pulse-wave sensor
on the basis of an intensity of a heart-rate signal contained in the pulse-wave signal filtered by the first filter unit, and
on the basis of a feedback light intensity that is detected by the pulse-wave-signal pulse-wave sensor.
(18) The vital sign processing device according to Item (17), in which
the light-intensity control unit sets, on the basis of the intensity of the heart-rate signal, at least one of a target value,
a lower-limit value, or
an upper-limit value of the feedback light intensity that is detected by the pulse-wave-signal pulse-wave sensor.

REFERENCE SIGNS LIST 10 sensor body portion
12 first PPG sensor
13 second PPG sensor
14 acceleration sensor
15, 17 controller
20 body-motion analysis unit
30 first noise-reduction processing unit
40 second noise-reduction processing unit
41 adaptive filter
50 reference-signal generating unit
52 adaptive-band-elimination-filter processing unit
54 second filter bank
60, 120 adaptive-band-pass-filter processing unit
62 first filter bank
70 heart-rate-fluctuation detection unit
80 heart-rate-trend detection unit
90 integration processing unit
100 stabilization processing unit
110 light-intensity control unit
200 heart-rate measurement device

The invention claimed is:

1. A vital sign processing device, comprising:
a pulse-wave sensor unit configured to output a pulse-wave signal;
a body-motion sensor configured to output a body-motion signal;
a noise-reduction processing unit configured to separate, based on the body-motion signal, a body-motion noise from the pulse-wave signal output from the pulse-wave sensor unit;
a plurality of calculation units configured to calculate a heart-rate-candidate information item and a reliability of the heart-rate-candidate information item based on the output pulse-wave signal, wherein
each of the plurality of calculation units is configured to calculate the heart-rate-candidate information item and the reliability of the heart-rate-candidate information item based on the pulse-wave signal from which the body-motion noise has been separated;
an output unit configured to output a heart-rate information item based on:
the output pulse-wave signal;
the calculated heart-rate-candidate information item, and
the reliability of the heart-rate-candidate information item; and
a first filter unit configured to:
set a first frequency band of the pulse-wave signal based on the output heart-rate information item, and
allow the set first frequency band of the pulse-wave signal to pass through the first filter unit.

2. The vital sign processing device according to claim 1, wherein the first filter unit is further configured to set the first frequency band based on a heart rate included in the heart-rate information item.

3. The vital sign processing device according to claim 2, wherein
the first filter unit includes a first filter bank including a plurality of band-pass filters, and
the first filter unit is further configured to select, based on the heart rate, a filter that allows the first frequency band to pass through the filter, wherein the filter is selected from the first filter bank.

4. The vital sign processing device according to claim 1, wherein
each of the plurality of calculation units is further configured to calculate the heart-rate-candidate information item and the reliability of the heart-rate-candidate information item based on the pulse-wave signal filtered by the first filter unit.

5. The vital sign processing device according to claim 1, wherein
the first filter unit is further configured to filter the pulse-wave signal from which the body-motion noise has been separated by the noise-reduction processing unit.

6. The vital sign processing device according to claim 1, wherein
the pulse-wave sensor unit includes a plurality of pulse-wave sensors, and
the pulse-wave sensor unit is further configured to output, as the pulse-wave signal, one of a plurality of pulse-wave-candidate signals generated by the plurality of pulse-wave sensors.

7. The vital sign processing device according to claim 6, further comprising
a generating unit configured to generate, based on the plurality of pulse-wave-candidate signals that are generated by the plurality of pulse-wave sensors, a reference signal to separate the body-motion noise, wherein
the noise-reduction processing unit includes an adaptive filter to which the reference signal is input as an input signal, and
the noise-reduction processing unit is further configured to output an error signal obtained by subtraction of an output value of the adaptive filter from the pulse-wave signal.

8. The vital sign processing device according to claim 7, further comprising
a second filter unit configured to:
set a second frequency band based on the heart-rate information item output by the output unit, and
remove the set second frequency band of the reference signal.

9. The vital sign processing device according to claim 8, wherein
the second filter unit is further configured to set the second frequency band based on a heart rate included in the heart-rate information item.

10. The vital sign processing device according to claim 9, wherein
the second filter unit includes a second filter bank including a plurality of band-elimination filters, and
the second filter unit is further configured to select, based on the heart rate, a filter that removes the second frequency band, wherein the filter is selected from the second filter bank.

11. The vital sign processing device according to claim 10, wherein
the second filter unit is further configured to filter at least one of the plurality of pulse-wave-candidate signals or the body-motion signal, and
the generating unit is further configured to generate the reference signal based on an output from the second filter unit.

12. The vital sign processing device according to claim 10, wherein
the generating unit is further configured to generate the reference signal based on the plurality of pulse-wave-candidate signals filtered by the first filter unit, and
the noise-reduction processing unit is further configured to output an error signal obtained by subtraction of the output value of the adaptive filter from the pulse-wave signal filtered by the first filter unit.

13. The vital sign processing device according to claim 12, wherein
the second filter unit is further configured to:
filter the reference signal generated by the generating unit, and
output the filtered reference signal to the adaptive filter.

14. The vital sign processing device according to claim 6, wherein
the plurality of pulse-wave sensors include a pulse-wave-signal pulse-wave sensor, wherein the pulse-wave-signal pulse-wave sensor is configured to:
generate the pulse-wave signal by emission of light beams in a specific predetermined wavelength band; and
detect a reflected light beam among the light beams in the specific wavelength band, and
the vital sign processing device further comprises:
a light-intensity control unit configured to control, based on the pulse-wave signal filtered by the first filter unit, light intensities of the light beams in the specific wavelength band, the light beams being emitted from the pulse-wave-signal pulse-wave sensor.

15. The vital sign processing device according to claim 14, wherein
the light-intensity control unit is further configured to control the light intensities of the pulse-wave-signal pulse-wave sensor based on
an intensity of a heart-rate signal contained in the pulse-wave signal filtered by the first filter unit, and
a feedback light intensity that is detected by the pulse-wave-signal pulse-wave sensor.

16. The vital sign processing device according to claim 15, wherein
the light-intensity control unit is further configured to set, based on the intensity of the heart-rate signal, at least one of
a target value,
a lower-limit value, or
an upper-limit value of the feedback light intensity that is detected by the pulse-wave-signal pulse-wave sensor.

17. A vital sign processing method, comprising:
generating, by a pulse-wave sensor, a pulse-wave signal;
outputting, by a body-motion sensor, a body-motion signal;
separating, by a noise-reduction processing unit, a body-motion noise from the generated pulse-wave signal, wherein the body motion noise is separated based on the body-motion signal;
calculating, by a plurality of calculation units, a heart-rate-candidate information item and a reliability of the heart-rate-candidate information item based on the generated pulse-wave signal, wherein
each of the plurality of calculation units calculates the heart-rate-candidate information item and the reliability of the heart-rate-candidate information item based on the pulse-wave signal from which the body-motion noise has been separated;
outputting a heart-rate information item based on:
the generated pulse-wave signal;
the calculated heart-rate-candidate information item, and
the reliability of the heart-rate-candidate information item;
setting, by a first filter unit, a first frequency band of the pulse-wave signal based on the output heart-rate information item; and
allowing, by the first filter unit, the set first frequency band of the pulse-wave signal to pass through the first filter unit.

18. An information processing device, comprising:
an acquisition unit configured to acquire a pulse-wave signal;
a body-motion sensor configured to output a body-motion signal;
a noise-reduction processing unit configured to separate, based on the body-motion signal, a body-motion noise from the acquired pulse-wave signal;
a plurality of calculation units configured to calculate a heart-rate-candidate information item and a reliability of the heart-rate-candidate information item based on the acquired pulse-wave signal, wherein
each of the plurality of calculation units is configured to calculate the heart-rate-candidate information item and the reliability of the heart-rate-candidate information item based on the pulse-wave signal from which the body-motion noise has been separated;
an output unit configured to output a heart-rate information item based on:
the acquired pulse-wave signal,
the calculated heart-rate-candidate information item, and
the reliability of the heart-rate-candidate information item; and
a first filter unit configured to:
set a first frequency band of the pulse-wave signal based on the output heart-rate information item, and
allow the set first frequency band of the pulse-wave signal to pass through the first filter unit.

* * * * *